(12) United States Patent
Saha et al.

(10) Patent No.: US 9,198,923 B2
(45) Date of Patent: Dec. 1, 2015

(54) PHOSPHATE MANAGEMENT WITH SMALL MOLECULES

(75) Inventors: Uttam Saha, Thornhill (CA); Christian F. Helvig, Markham (CA); P. Martin Petkovich, Kingston (CA)

(73) Assignee: OPKO IRELAND GLOBAL HOLDINGS, LTD., Grand Cayman (KY)

( * ) Notice: Subject to any disclaimer, the term of this patent is extended or adjusted under 35 U.S.C. 154(b) by 446 days.

(21) Appl. No.: 13/146,217

(22) PCT Filed: Jan. 26, 2010

(86) PCT No.: PCT/CA2010/000111
§ 371 (c)(1),
(2), (4) Date: Oct. 19, 2011

(87) PCT Pub. No.: WO2010/083613
PCT Pub. Date: Jul. 29, 2010

(65) Prior Publication Data
US 2012/0028926 A1 Feb. 2, 2012

Related U.S. Application Data

(60) Provisional application No. 61/147,348, filed on Jan. 26, 2009.

(51) Int. Cl.
| | | |
|---|---|---|
| *A61K 31/66* | (2006.01) | |
| *A61K 31/662* | (2006.01) | |
| *A61K 31/663* | (2006.01) | |
| *A61K 31/675* | (2006.01) | |
| *A61K 45/06* | (2006.01) | |

(52) U.S. Cl.
CPC ............. *A61K 31/66* (2013.01); *A61K 31/662* (2013.01); *A61K 31/663* (2013.01); *A61K 31/675* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,880,584 A | * | 4/1975 | Redmore .................. 422/7 |
| 4,806,532 A | | 2/1989 | Dousa |
| 5,597,815 A | * | 1/1997 | Deluca et al. .............. 514/167 |
| 6,355,823 B1 | | 3/2002 | Peerce |
| 6,787,528 B2 | | 9/2004 | Peerce |
| 7,109,184 B2 | | 9/2006 | Jozefiak et al. |
| 7,119,120 B2 | | 10/2006 | Jozefiak et al. |
| 7,691,898 B2 | | 4/2010 | Tomiyama et al. |
| 2006/0280719 A1 | | 12/2006 | Jozefiak et al. |
| 2007/0021509 A1 | | 1/2007 | Jozefiak et al. |
| 2008/0119441 A1 | * | 5/2008 | Tomiyama et al. ......... 514/80 |
| 2008/0262285 A1 | * | 10/2008 | Black et al. ................ 588/318 |

FOREIGN PATENT DOCUMENTS

| | | |
|---|---|---|
| EP | 1813620 A1 | 8/2007 |
| WO | WO-03/048134 A1 | 6/2003 |
| WO | WO-03/057225 A1 | 7/2003 |
| WO | WO-03/080630 A1 | 10/2003 |
| WO | WO-2004/085448 A2 | 10/2004 |
| WO | WO-2006/038719 A1 | 4/2006 |

OTHER PUBLICATIONS

"Inhibition of human intestinal brush border membrane vesicle Na+-dependent phosphate uptake by phosphophloretin derivatives" by Peerce et al., Biochem. Biophys. Res. Comm. 301, 8-12 (2003).*
Supplementary European Search Report for European Application No. EP 10733188, dated Jun. 28, 2012.
Elder Grahame J: "Targets for phosphate control in chronic kidney disease", Nephrology, Feb. 2004, vol. 9, No. 1, pp. 2-6.
International Search Report and Written Opinion for corresponding International application No. PCT/CA2010/000111, dated Jun. 15, 2010.
Peerce et al., Inhibition of human intestinal brush border membrane vesicle Na+-dependent phosphate uptake by phosphophloretin derivatives, Biochem. Biophys. Res. Commun., 301:812 (2003). [Abstract only provided.].

* cited by examiner

*Primary Examiner* — Theodore R West
(74) *Attorney, Agent, or Firm* — Marshall, Gerstein & Borun LLP

(57) ABSTRACT

This invention relates to methods and small molecules having a phosphate group that can be used to inhibit phosphate transport and to treat or prevent diseases that are related to disorders in the maintenance of normal serum phosphate levels.

19 Claims, 7 Drawing Sheets

PHOSPHATE MANAGEMENT WITH SMALL MOLECULES

CROSS-REFERENCE TO RELATED APPLICATIONS

This is the U.S. national phase of International Application No. PCT/CA2010/000111, filed Jan. 26, 2010, which claims the benefit of U.S. Provisional Patent Application Ser. No. 61/147,348, filed Jan. 26, 2009, the entire disclosures of which are hereby incorporated herein by reference.

BACKGROUND

1. Field of the Disclosure

The disclosure relates generally to methods and small molecules that can be used to inhibit phosphate transport. Particularly, the disclosure is directed to methods and small molecules that can be used to treat or prevent diseases that are related to disorders in the maintenance of normal serum phosphate levels. More particularly, this disclosure is directed to methods and small molecules that can be used to treat or prevent hyperphosphatemia.

2. Brief Description of Related Technology

Phosphorus and inorganic phosphate (Pi) participate in numerous critical biological processes including cell signaling, nucleic acid synthesis, energy metabolism, membrane function, and bone mineralization. Thus, significant changes in serum Pi levels or an offset Pi balance can have significant physiological consequences. Rapid decreases in serum Pi concentrations can be manifested in a number of pathologies including myopathy, cardiac dysfunction, abnormal neutrophil function, platelet dysfunction, and red-cell membrane fragility. Chronic serum Pi deficiency can cause impairment in bone mineralization, which can lead to osteomalacia and rickets. In contrast, elevated serum Pi concentrations contribute to the pathogenesis of secondary hyperparathyroidism in patients with chronic renal failure. Hyperphosphatemia and the consequent increase in calcium-phosphate (CaxP) product results in the calcification of soft tissues and blood vessel walls, and is associated with a higher risk of mortality.

The plasma level of Pi is established mainly through: (1) the control of Pi absorption in the small intestine, which is directly stimulated by vitamin D, (2) factors controlling the rate of bone resorption, and (3) Pi excretion in the kidney, which is under the influence of the parathyroid hormone (PTH) and phosphaturic factors such as fibroblast growth factor-23 (FGF-23). Disturbances of signal pathways controlling phosphate homeostasis, such as inadequate renal function or hypoparathyroidism, often give rise to hyperphosphatemia. Chronic hyperphosphatemia can lead to severe abnormalities in calcium and phosphorus metabolism, which is often manifested by hyperparathyroidism, bone disease and ectopic calcification in joints, lungs, eyes and vasculature. For patients who exhibit renal insufficiency, an elevation of serum phosphorus within the normal range has been associated with the progression of renal failure and an increased risk of cardiovascular events. Conversely, reducing phosphate retention can slow the progression of kidney disease. Thus, for renal failure patients who are hyperphosphatemic and for chronic kidney disease (CKD) patients whose serum phosphate is within the normal range or is only slightly elevated, therapeutic approaches to reduce phosphate uptake and retention are beneficial.

As chronic kidney disease progresses, serum phosphate levels become more difficult to control. More than 60% of patients on hemodialysis were reported to have serum phosphate levels exceeding 5.5 mg/dL. A normal physiological serum phosphorus concentration is generally considered to be between about 2.5 mg/dl to about 4.5 mg/dl (Block G & Port F, Am. J. Kidhey Dis. 2000, 35:1226-1237). Furthermore, hemodialysis patients with serum phosphorus levels greater than 6.5 mg/dL were reported to have a 27% higher mortality risk than patients with serum phosphorus between 2.4 and 6.5 mg/dL. Based on these findings, the National Kidney Foundation—Kidney Disease Outcome Quality Initiative (KJ-DOQI) Clinical Practice Guidelines for Bone Metabolism and Disease in Chronic Kidney Disease have recently recommended more stringent actions for controlling serum phosphorus and CaxP product in order to improve patients' quality of life and longevity.

Current therapeutic approaches to manage hyperphosphatemia include limiting dietary phosphorus intake and employing phosphate binding matrices, both of which are largely inadequate and often poorly tolerated. Early clinical emphasis was directed toward limiting dietary phosphorus intake. Dietary phosphorus comes from three major sources, the inherent phosphorus content in foodstuff, phosphate-containing additives for preservation, and phosphate-containing dietary supplements. Because dietary phosphorus is mainly derived from protein, significant restriction of phosphorus inevitably limits protein intake. As a result, dialysis patients experience an increased risk of malnutrition and mortality.

Phosphate binding matrices initially used were aluminum and calcium compounds. Calcium salts that have been utilized for phosphate binding include calcium carbonate, acetate (such as PhosLo® calcium acetate tablets), citrate, alginate, and ketoacid salts. The advantages of using calcium as the primary phosphate complexing substance are inhibitory effects on parathyroid hormone secretion, low cost, and good tolerability. However, this class of therapeutics generally results in hypercalcemia because such binders can raise the CaxP index, leading to the manifestations of elevated phosphorus. Aluminum and magnesium salts are available as non-calcium-based phosphate binders, but these compounds have a number of potentially severe side effects. Prolonged used of aluminum gels leads to accumulations of aluminum, and often to aluminum toxicity, accompanied by such symptoms as encephalopathy, osteomalacia, and myopathy.

Polymeric resins, initially developed as bile acid sequestrants, are also being studied or used clinically as Pi binders. Reduced progression or even improvement of vascular calcifications was demonstrated with the use of these polymer-based phosphate binders. However, inherent in their ability to bind cholesterol, these binders also complex and therefore deplete vitamin D, among other important vitamins and nutrients. Lanthanum chloride, a non-calcium-based phosphate binder has also been clinically investigated. The effect on phosphate levels appears to be similar to those of polymer-based phosphate binders. Iron-oxide, because of its ability to complex phosphate is also being used in the clinic. All of the current therapies are based on the complexing of dietary phosphate to make it inaccessible for cross-luminal transport into serum.

For the foregoing reasons, there remains a need for new methods and pharmaceutical compositions to reduce phosphate absorption in the GI tract and to prevent or to attenuate hyperphosphatemia.

SUMMARY

One aspect of the disclosure provides a method for inhibiting the transport of phosphate across the membrane of human epithelial cells, and hence the gastrointestinal absorption of phosphate, by administering a small molecule having a phosphate group, or any formulation comprising a small molecule having a phosphate group disclosed herein.

Another aspect of the disclosure provides a method for preventing, stabilizing, or reversing the progress of diseases associated with disorders in phosphate metabolism or impaired phosphate transport by administering a small molecule having a phosphate group, or any formulation comprising a small molecule having a phosphate group disclosed herein.

Another aspect of the disclosure provides a method for the treatment or prevention of diseases wherein the accumulation of phosphate in serum can occur by administering a small molecule having a phosphate group, or any formulation comprising a small molecule having a phosphate group disclosed herein.

Another aspect of the disclosure provides a method for treating, delaying, or preventing hyperphosphatemia arising as a result of pharmaceutical intervention for the treatment of diseases in need of such therapy by administering a small molecule having a phosphate group, or any formulation comprising a small molecule having a phosphate group disclosed herein.

Another aspect of the disclosure relates to small molecules having a phosphate group represented by Compounds 001-029 and Structural Formulas I-XXXII. These compounds can inhibit the transport of phosphate across the membrane of human epithelial cells, and hence can inhibit the gastrointestinal absorption of phosphate. These compounds can be used to treat or prevent diseases whose root cause or effect are related to disorders in the maintenance of normal serum phosphate levels.

Another aspect of the disclosure relates to the administration of small molecules having a phosphate group described herein. These small molecules can be administered alone or in combination in an acceptable pharmaceutical formulation, orally or by injection.

For the compositions and methods described herein, preferred features, such as components, compositional ranges thereof, substituents, conditions, and steps, can be selected from the various examples provided herein.

Further aspects and advantages will be apparent to those of ordinary skill in the art from a review of the following detailed description, taken in conjunction with the figures. While the methods, compounds, and compositions are susceptible of embodiments in various forms, the description hereafter includes specific embodiments with the understanding that the disclosure is illustrative, and is not intended to limit the invention to the specific embodiments described herein.

It should be understood that the phraseology and terminology used herein are for the purpose of description and should not be regarded as limiting. The use of the terms "including," "having" and "comprising" and variations thereof herein is meant to encompass the items listed thereafter and equivalents thereof as well as optional additional items and equivalents thereof.

DETAILED DESCRIPTION

Figure 1A:
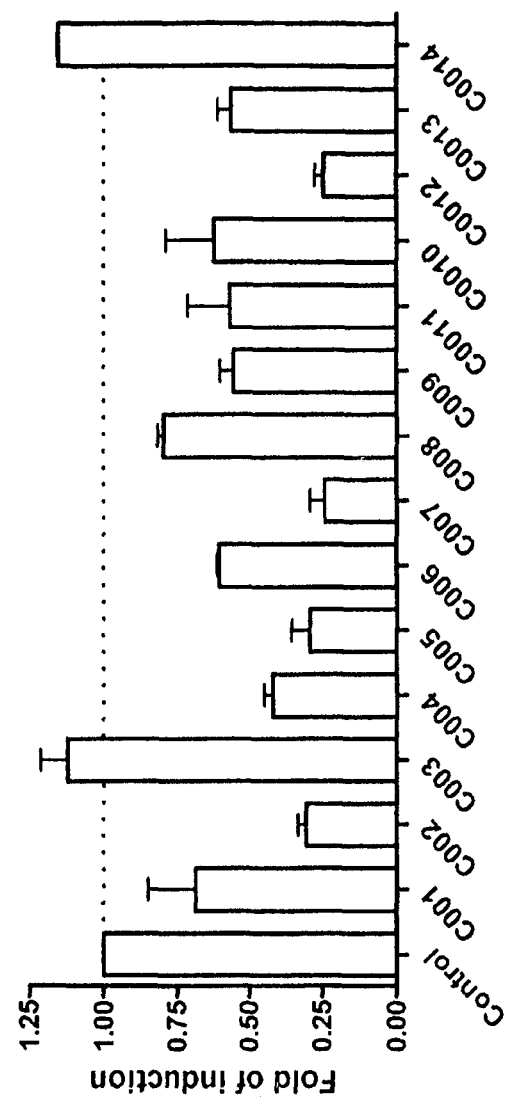
FIG. 1 shows the effect of Compounds 001-029 on phosphate uptake inhibition in Caco-2 human intestinal epithelial cells.

Without intending to be bound by any particular theory, a more effective approach to limiting phosphate absorption (instead of restricting dietary intake of phosphate or using phosphate binding matrices) is by directly blocking intestinal alkaline phosphatase activity responsible for intestinal phosphate production and by inhibiting the cross-luminal transport system (NaPi-2b) responsible for delivering phosphate into the serum. Phosphate absorption in the small intestine can be carrier-mediated, coupling the transport of phosphate to that of sodium in an energy-dependent mechanism. An example is the case of the NaPi-2b Na/phosphate co-transporter. Other mechanisms, however, may also be important for transport. The identification of small molecule inhibitors of phosphate transport can be used therapeutically to limit intestinal phosphate absorption from nutritional sources. This approach can be useful, for example, for the treatment or prevention of hyperphosphatemia in patients with renal disease.

In describing the embodiments and claiming the invention, the following terminology are used in accordance with the definitions set forth below, unless explicitly characterized otherwise.

As used herein, the term "inhibiting" means reducing or preventing, in whole or in part.

As used herein, the term "preventing" means achieving a prophylactic benefit. For example, a small molecule compound having a phosphate group is administered to a patient at risk of developing hyperphosphatemia or to a patient reporting one or more of the pathophysiological symptoms of hyperphosphatemia even though a diagnosis of hyperphosphatemia may not have been made. Specifically, a small molecule compound having a phosphate group can be administered to a patient with chronic kidney disease wherein hyperphosphatemia has not been diagnosed.

As used herein, a "pharmaceutically acceptable formulation" refers to a molecular entity or composition that is approved or approvable by the U.S. Food and Drug Administration or a corresponding foreign regulatory agency for administration to humans.

As used herein, an "effective amount" is an amount that results in a beneficial therapeutic outcome of the condition being treated. For example, an effective amount of a small molecule having a phosphate group will have one or more effects such as lowering the serum phosphorus levels in a subject having hyperphosphatemia, preventing serum phosphorus levels from rising in a subject having or at risk of having hyperphosphatemia, or reducing the absorption of phosphorus from food which can be measured, for example, by increased fecal phosphorus or by lowered or stabilized serum phosphorus level.

As used herein "beneficial therapeutic outcome" includes amelioration or eradication of the underlying disorder being treated, not withstanding that the subject may still be afflicted with the underlying disorder. In a subject having hyperphosphatemia, a beneficial therapeutic outcome includes amelioration or eradication of the underlying hyperphosphatemia.

For example, the subject having hyperphosphatemia would experience a decrease in the severity of symptoms, including decreased levels of serum phosphate, or a delay in the onset of symptoms associated with the cause or effect of elevated serum phosphate levels. Such symptoms comprise soft tissue ectopic calcification, cardiovascular calcification, cardiovascular events, renal deterioration, calciphalaxis, hyperparathyroidism, uremic bone disease, renal bone disease, osteoporosis, and hyperphosphatemia.

As used herein, "subjects in need of treatment" include subjects that currently have or may develop diseases and or conditions that can be treated with phosphate transport inhibitors to achieve a beneficial therapeutic outcome. A contemplated subset of such subjects are subjects who have been diagnosed with a disease or condition that can be treated with phosphate transport inhibitors to achieve a beneficial therapeutic outcome.

As used herein, a "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the therapeutic compositions, its use in therapeutic compositions is contemplated. Supplementary active ingredients also can be incorporated into the compositions.

As used herein, "excipient" refers to carriers, solvents, stabilizers, adjuvants, diluents, etc., depending upon the particular mode of administration and dosage form, for administration of a pharmaceutical agent, such as the compounds described herein.

As used herein, "hyperphosphatemia" is used broadly to describe a condition in a subject wherein serum phosphorus is present at a concentration above the medically accepted normal range.

As used herein, the term "alkyl" refers to straight chained and branched saturated hydrocarbon groups, nonlimiting examples of which include methyl, ethyl, and straight chain and branched propyl and butyl groups. Alkyl groups can have, for example, from 1 to 20 carbon atoms, from 1 to 10 carbon atoms, and/or from 1 to 6 carbon atoms.

As used herein, the term "dialkyl" refers to alkyl groups that are attached to the same atom. For example N-dialkyl refers to two alkyl groups that are each bonded to the same nitrogen atom.

As used herein, the term "aryl" refers to a monocyclic or polycyclic aromatic group, preferably a monocyclic or bicyclic aromatic group. Unless otherwise indicated, an aryl group can be unsubstituted or substituted with one or more, and in particular one to four, groups independently selected from, for example, halo, alkyl, alkenyl, —$OCF_3$, —$NO_2$, —CN, —NC, —OH, alkoxy, amino, —$CO_2H$, —$CO_2$-alkyl, aryl, and heteroaryl groups. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, —$OCF_3$, —$NO_2$, —CN, —NC, —OH, alkoxy, amino, —$CO_2H$, —$CO_2$-alkyl, aryl, and heteroaryl. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

As used herein, the term "benzyl" refers to an aromatic group attached to a methylene. Unless otherwise indicated, a benzyl group can be unsubstituted or substituted with one or more substituents, selected from, for example, halo, alkyl, alkenyl, —$OCF_3$, —$NO_2$, —CN, —NC, —OH, alkoxy, amino, —$CO_2H$, —$CO_2$-alkyl, aryl, aromatic and heteroaryl groups. An example of a benzyl group is —$CH_2$—$C_6H_5$.

As used herein, the term "methylene" refers to a carbon that is attached to two hydrogen atoms.

As used herein, the term "halogen" refers to the halogens of Group VITA of the periodic table, including F, Cl, Br, and I.

As used herein, the abbreviations identified in Table 1 below designate the corresponding chemical name identified in Table 1, unless explicitly indicated otherwise in context:

TABLE 1

| Abbreviation | Chemical Name |
| --- | --- |
| AcOH | Acetic acid |
| n-BuLi | n-Butyllithium |
| $CaCl_2$ | Calcium chloride |
| $CCl_4$ | Carbon tetrachloride |
| DCM | Dichloromethane |
| DIPA | Diisopropylamine |
| DIPEA | Diisopropylethylamine |
| DMEM | Dulbecco's Modified Eagle's Medium |
| DMF | N,N-Dimethylformamide |
| DMSO | Dimethyl sulfoxide |
| dppb | 1,4-bis-(Diphenylphosphino)butane |
| EDTA | Ethylenediaminetetraacetic acid |
| $Et_2O$ | Diethyl ether |
| EtOAc | Ethyl acetate |
| EtOH | Ethanol |
| HPLC | High performance liquid chromatography |
| KCl | Potassium chloride |
| MeOH | Methanol |
| $MgSO_4$ | Magnesium sulfate |
| $NaBH_4$ | Sodium borohydride |
| $Na_2SO_4$ | Sodium sulfate |
| $NH_4Cl$ | Ammonium chloride |
| NMR | Nuclear magnetic resonance |
| PBS | Phosphate buffered saline |
| PhMgBr | Phenyl magnesium bromide |
| PMA | Phosphomolybdic acid |
| rt | Room Temperature |
| $R_f$ | Retention factor |
| TEA | Triethylamine |
| THF | Tetrahydrofuran |
| TLC | Thin layer chromatography |
| TMS-Br | Trimethylsilyl bromide |
| Tris-HCl | 2-Amino-2-(hydroxymethyl)-1,3-propanediol, hydrochloride |
| UV | Ultraviolet |

Methods

A first method contemplated is a method for inhibiting phosphate transport across the membrane of human epithelial cells and hence, gastrointestinal absorption of phosphate. The method comprises the step of administering to a human subject in need of phosphate transport inhibition, a small molecule having a phosphate group in an amount effective to achieve a beneficial therapeutic outcome. Preferably, the small molecule having a phosphate group will be in a pharmaceutically acceptable formulation.

Another method contemplated is a method for inhibiting phosphate transport across the membrane of human epithelial cells and hence, gastrointestinal absorption of phosphate. The method comprises the step of administering to a human subject in need of phosphate transport inhibition, a pharmaceutically acceptable formulation that includes a small molecule having a phosphate group in an amount effective to achieve a beneficial therapeutic outcome.

Another method contemplated is a method for preventing, stabilizing, or reversing the progress of diseases associated with disorders in phosphate metabolism or impaired phosphate transport such as, but not limited to, hyperparathyroidism, metabolic bone disease, uremic bone disease, renal bone disease, soft tissue calcification, cardiovascular calcification, cardiovascular events, calciphylaxis, and osteoporosis. The method comprises the step of administering to a human subject having a disease associated with disorders in phosphate metabolism or impaired phosphate transport, a small molecule having a phosphate group, or any formulation comprising a small molecule having a phosphate group disclosed herein, in an amount effective to prevent, stabilize, or reverse the progress of the disease associated with phosphate metabolism or impaired phosphate transport.

Another method contemplated is a method for the treatment or prevention of diseases wherein the accumulation of phosphate in serum can occur. Such diseases include but are not limited to hyperphosphatemia, chronic kidney disease, secondary hyperparathyroidism, hyperparathyroidism, and hypoparathyroidism. The method comprises the step of administering to a human subject in need of serum phosphate reduction or serum phosphate maintenance, a small molecule having a phosphate group, or any formulation comprising a small molecule having a phosphate group disclosed herein, in an amount effective to reduce or maintain serum phosphate levels.

Another method contemplated is a method for treating, delaying, or preventing hyperphosphatemia arising as a result of pharmaceutical intervention, such as vitamin D based therapy, for the treatment of diseases in need of such therapy, such as secondary hyperparathyroidism. The method comprises the step of administering to a human subject having pharmaceutical intervention for the treatment of a disease in need of such intervention a small molecule having a phosphate group, or any formulation comprising a small molecule having a phosphate group disclosed herein, in an amount effective to treat, delay, or prevent hyperphosphatemia.

For any of the methods disclosed herein, the small molecule having a phosphate group can be administered alone, or alternatively can be administered in combination with one or more additional small molecules having a phosphate group.

Small Molecule Compounds Having a Phosphate Group

Yet another aspect of the present invention relates to small molecules having a phosphate group. Examples of small molecules having a phosphate group include, but are not limited to, Compounds 001-029 described in Table 2.

TABLE 2-continued
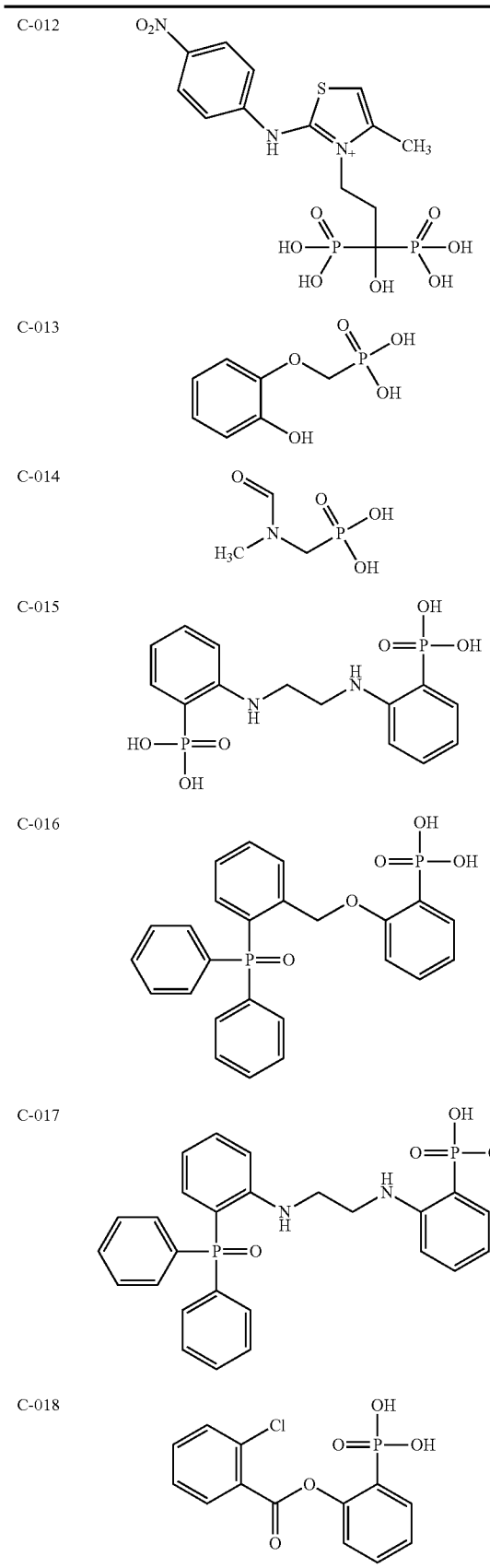
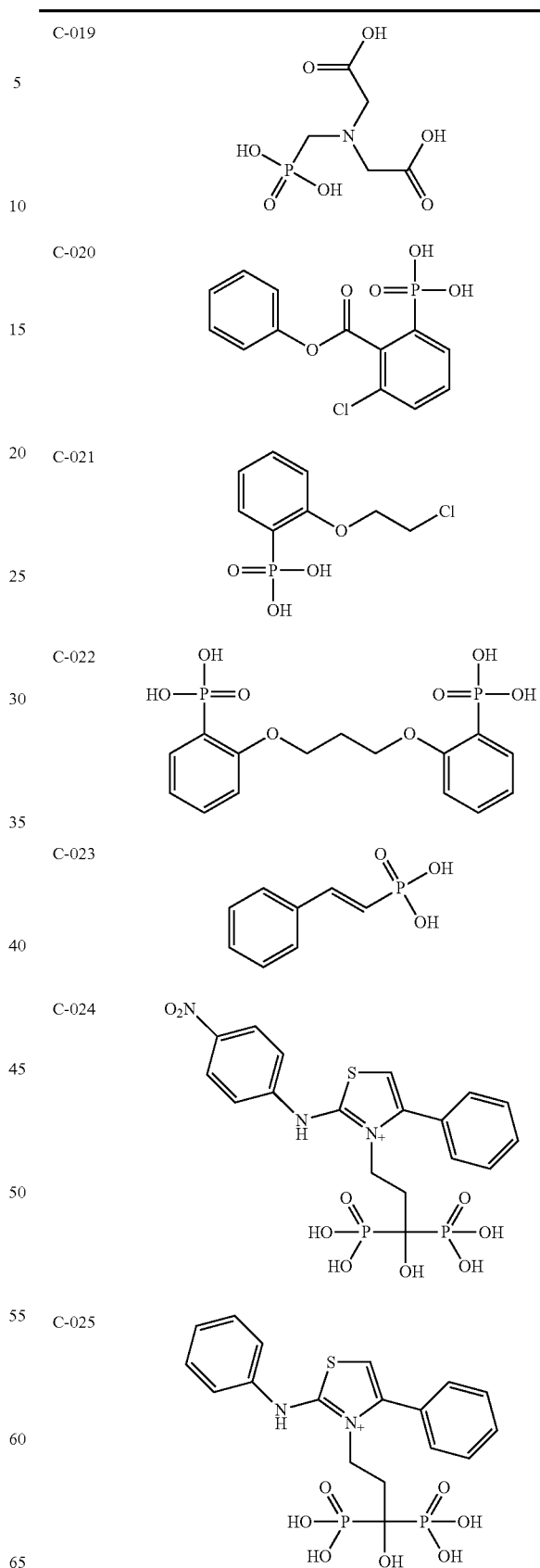

TABLE 2-continued

C-026
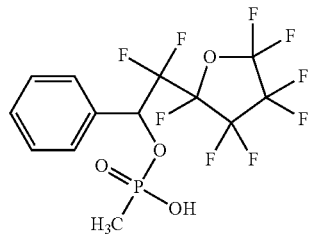 [SMILES: CP(=O)(O)OC(c1ccccc1)C(F)(F)C1(F)OC(F)(F)C(F)(F)C1(F)F]

C-027
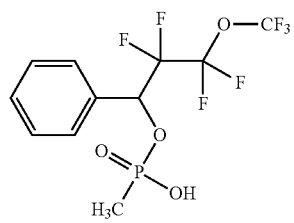 [SMILES: CP(=O)(O)OC(c1ccccc1)C(F)(F)C(F)(F)OC(F)(F)F]

C-028
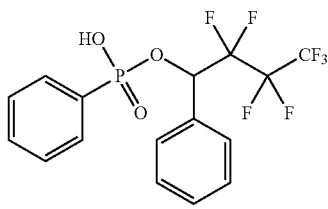 [SMILES: O=P(O)(OC(c1ccccc1)C(F)(F)C(F)(F)C(F)(F)F)c1ccccc1]

C-029
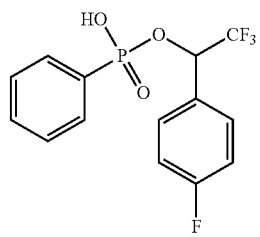 [SMILES: O=P(O)(OC(c1ccc(F)cc1)C(F)(F)F)c1ccccc1]

In one embodiment, the small molecule having a phosphate group is selected from Structural Formulas I-VII, wherein X=O, S, NH, or N-alkyl; $R^1$=halogen, OH, O-alkyl, N-dialkyl, or NHCO-alkyl at single or multiple positions; and $R^2$=H, alkyl, or substituted benzyl.

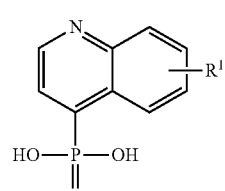

I

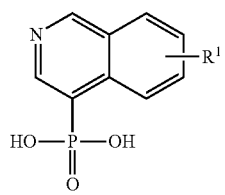

II

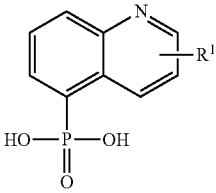

III

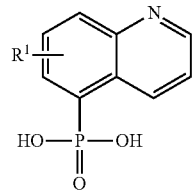

IV

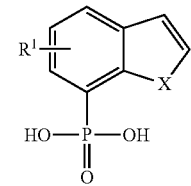

V

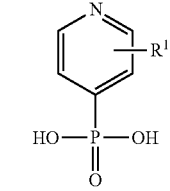

VI

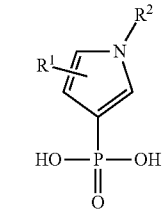

VII

In another embodiment, the small molecule having a phosphate group is selected from Structural Formulas VIII-XI, wherein $R^3$=halogen, alkyl, substituted benzyl, OH, O-alkyl, N-dialkyl, or NHCO-alkyl at single or multiple positions The position of the N-atom can vary. For example, the N-atom is part of the aromatic ring that contains the phosphate substituent in Compound IX, but is not part of the aromatic ring that contains the phosphate substitutent in Compound XI.

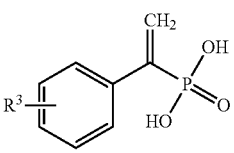

VIII

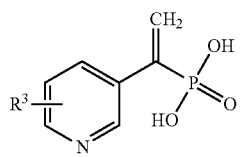

IX

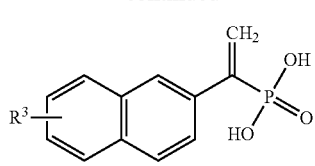

X

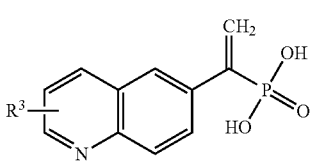

XI

In another embodiment, the small molecule having a phosphate group is selected from Structural Formulas XII-XIII, wherein $R^4$=H, halogen, O-alkyl, S-alkyl, N-dialkyl, or NHCO-alkyl; and n=0, 1, or 2.

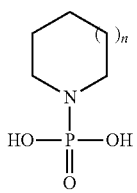

XII

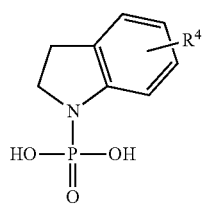

XIII

In another embodiment, the small molecule having a phosphate group is selected from Structural Formula XIV, wherein $R^1$=halogen, OH, O-alkyl, N-dialkyl, or NHCO-alkyl; $R^5$=alkyl, aryl, or substituted aryl; and m=1 to 6 carbon atoms.

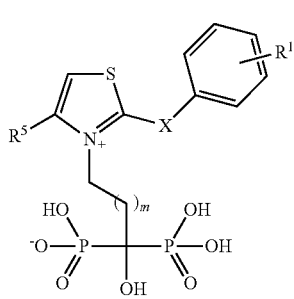

XIV

In another embodiment, the small molecule having a phosphate group is selected from Structural Formula XV, wherein $R^6$=alkyl, benzyl, or aromatic substituted benzyl.

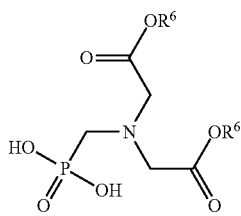

XV

In another embodiment, the small molecule having a phosphate group is selected from Structural Formula XVI, wherein $R^7$=H, alkyl, benzyl, or aromatic substituted benzyl.

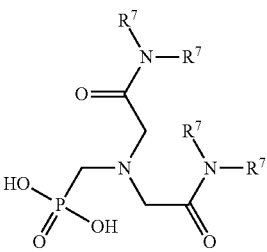

XVI

In another embodiment, the small molecule having a phosphate group is selected from Structural Formulas XVII-XVIII, wherein $R^8$=H, alkyl, aryl, benzyl, or aromatic substituted benzyl; and m=1 carbon atom or higher, preferably 1 to 6 carbon atoms.

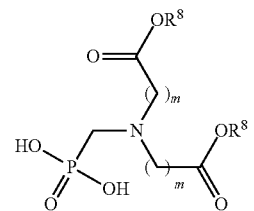

XVII

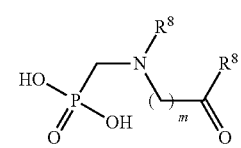

XVIII

In another embodiment, the small molecule having a phosphate group is selected from Structural Formulas XIX-XXI, wherein Y=O or S; $R^1$=OH, O-alkyl, halogen, N-dialkyl, or NHCO-alkyl; $R^9$=H or alkyl; and n=0, 1, or 2.

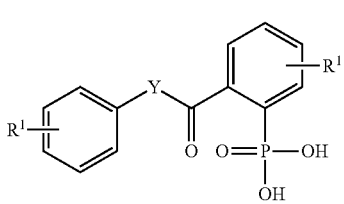

XIX

-continued

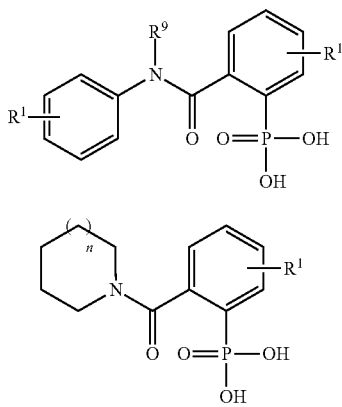

XX

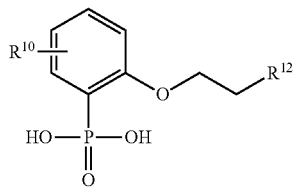

XXI

In another embodiment, the small molecule having a phosphate group is selected from Structural Formula XXII, wherein $R^{10}$=alkyl, O-alkyl, S-alkyl, aryl, $NR^{11}_2$, or $NCOR^{11}$; $R^{11}$ is alkyl or aryl; and $R^{12}$=halogen.

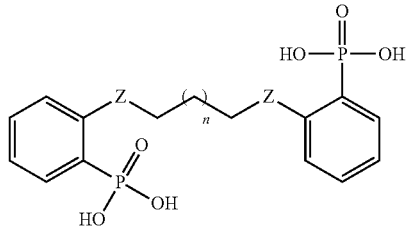

XXII

In another embodiment, the small molecule having a phosphate group is selected from Structural Formula XXIII, wherein each Z is independently O, S, N, or $CH_2$, and n=0, 1 or 2.

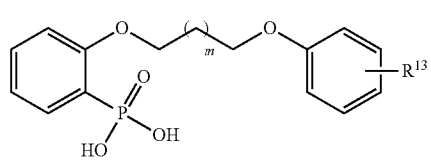

XXIII

In another embodiment, the small molecule having a phosphate group is selected from Structural Formula XXIV, wherein $R^{13}$=halogen, $OR^{14}$, $NR^{15}_2$, $PO_3H_2$, $SO_3H$, COOH, or $NH_2$; $R^{14}$=methyl, ethyl, isopropyl, tert-butyl, allyl, or substituted benzyl, or unsubstituted benzyl; $R^{15}$=methyl, ethyl, isopropyl, allyl, or benzyl, substituted benzyl, or unsubstituted benzyl; and m=1 to 6 carbon atoms.

XXIV

In another embodiment, the small molecule having a phosphate group is selected from Structural Formula XXV, wherein

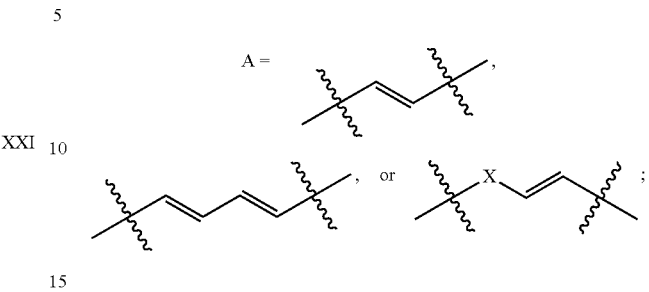

X=O, S, NH, or N-alkyl; and $R^{16}$=$SO_3H$, COOH, or $NH_2$.

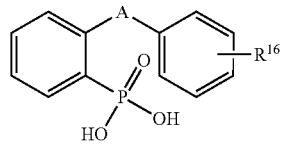

XXV

In another embodiment, the small molecule having a phosphate group is selected from Structural Formulas XXVI-XXVII wherein $R^{17}$=methyl, ethyl, isopropyl, tert-butyl, cyclohexyl, aryl, or heteroaryl, preferably benzene, pyridyl, or benzyl; and $R^{18}$=methyl, ethyl, isopropyl, tert-butyl, halogen, OH, O-alkyl, N-dialkyl or NHCO-alkyl at single or multiple positions.

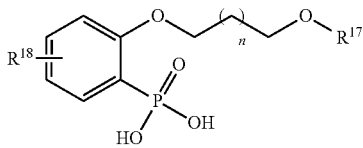

XXVI

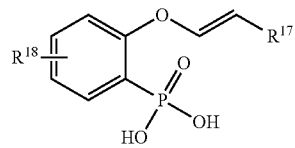

XXVII

In another embodiment, the small molecule having a phosphate group is selected from Structural Formula XXVIII wherein $R^{19}$=halogen, $NR^{11}_2$, $NHCOR^{11}$, $SR^{11}$ or heteraryl; $R^{20}$=halogen, methyl, ethyl, isopropyl, tert-butyl, $N(CH_3)_2$, $N(Et)_2$, $N(iPr)_2$, $NHCOCH_3$, $NHCOCF_3$, or NHCOPh; $R^{11}$=alkyl or aryl; and n=0, 1, or 2.

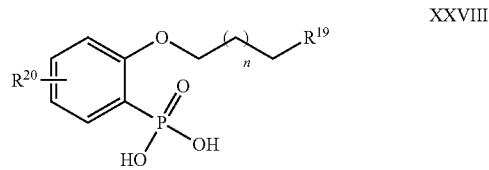

XXVIII

In another embodiment, the small molecule having a phosphate group is selected from Structural Formulas XXIX-XXXI, wherein $R^{10}$=alkyl, O-alkyl, S-alkyl, aryl, $NR^{11}_2$, or $NCOR^{11}$; wherein $R^{11}$=alkyl or aryl.

XXIX

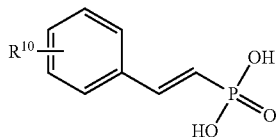

XXX

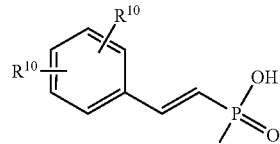

XXXI

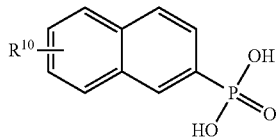

In another embodiment, the small molecule having a phosphate group is selected from Structural Formula XXXII, wherein $R^{21}$=alkyl, halogenated alkyl, O-alkyl, substituted aryl, or heteroaryl; $R^5$=alkyl, aryl, or substituted aryl; n=0, 1, or 2.

XXXII

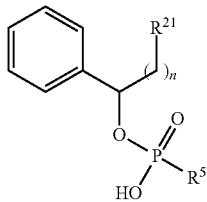

The small molecules having a phosphate group, including Compounds 001-029 and those represented by Structural Formulas I-XXXII, can be used to inhibit the transport of phosphate across the membrane of human epithelial cells, and hence the gastrointestinal absorption of phosphate. These small molecules having a phosphate group can also be used to treat or prevent diseases whose root cause or effect is related to disorders in the maintenance of normal serum phosphate levels as described herein.

Formulations and Dosing of the Small Molecule Having a Phosphate Group

The small molecule having a phosphate group, alone or in combination, can be prepared for administration orally as a dietary formulation such as, but not limited to an elixir, liquid, gel, syrup, slurry, or in the form of capsules, tablets, or pills. The compounds, alone or in combination, can be injected in a formulation suitable for injection either subcutaneously, intravenously or intraperitoneally.

The small molecule having a phosphate group can be administered in a pharmaceutical formulation comprising one or more of the small molecules having a phosphate group and a pharmaceutically acceptable carrier, diluent, or excipient.

The small molecule having a phosphate group can be administered alone or in combination in an acceptable pharmaceutical formulation to reduce or limit the accumulation of phosphate in a human subject by reducing the uptake of phosphate from the digestive tract and/or increasing the rate of phosphate excretion in urine in subjects in need of such intervention therapeutically or prophylactically.

For purposes of the invention, the amount or dose of the small molecule having a phosphate group administered, or pharmaceutical formulation thereof, should be sufficient to effect, e.g., a therapeutic or prophylactic response, in the human subject over a reasonable time frame. The dose will be determined by the efficacy of the particular small molecule having a phosphate group and the condition of the human subject, as well as the body weight of the human subject to be treated.

The dose of the small molecule having a phosphate group, or pharmaceutical formulation thereof, will also be determined by the existence, nature, and extent of any adverse side effects that might accompany the administration of a particular small molecule having a phosphate group or pharmaceutical formulation thereof. Typically, the attending physician will decide the dosage of the small molecule having a phosphate group with which to treat each individual patient, taking into consideration a variety of factors, such as age, body weight, general health, diet, sex, the small molecule having a phosphate group to be administered, route of administration, and the severity of the condition being treated. By way of example and not intending to limit the invention, the dose of the small molecule having a phosphate group or pharmaceutical formulation thereof can be about 0.0001 to about 1 g/kg body weight of the subject being treated/day, from about 0.0001 to about 0.001 g/kg body weight/day, or about 0.01 mg to about 1 g/kg body weight/day.

EXAMPLES

The following examples are provided for illustration and are not intended to limit the scope of the invention.

Example 1

Figure 1B:
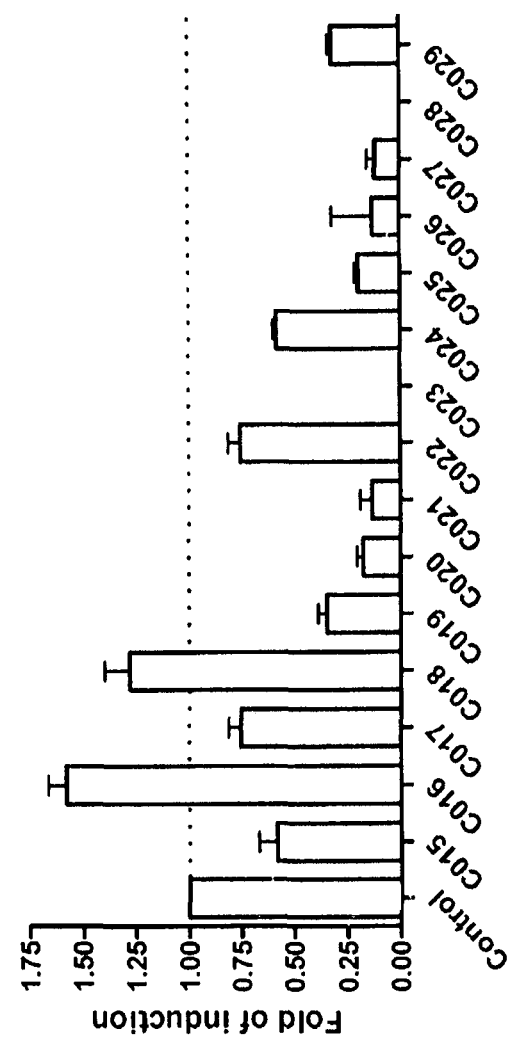
Figure 2A:
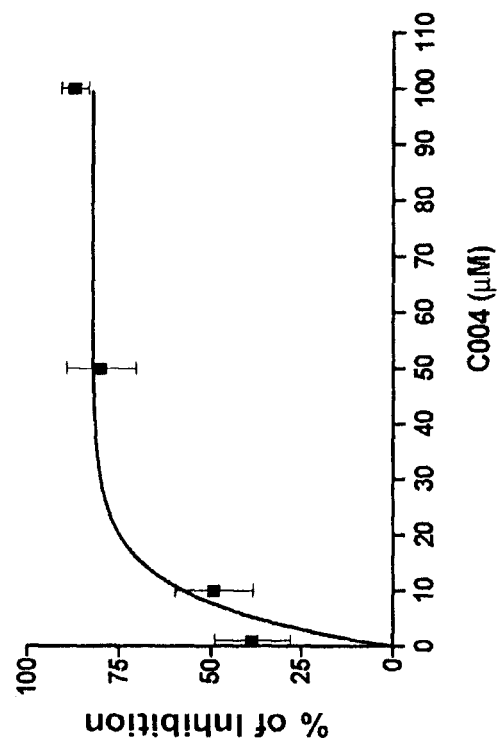
FIG. 2 shows the dosage effect of Compounds 002, 004, 012, and 028 on phosphate uptake inhibition in Caco-2 human intestinal epithelial cells.
Figure 2B:
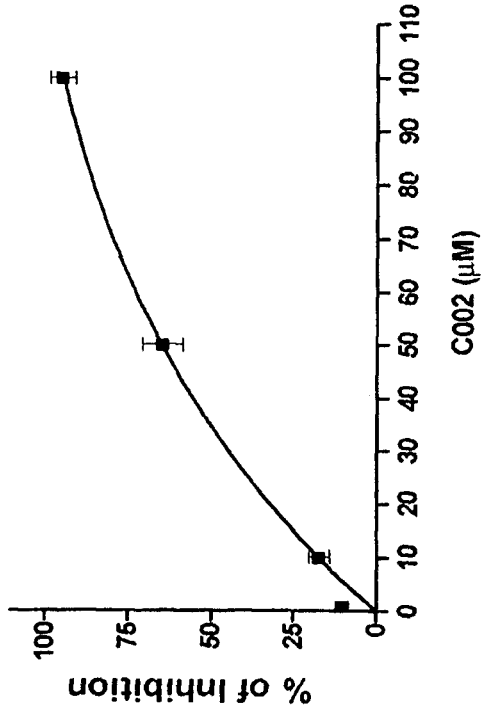
Figure 2D:
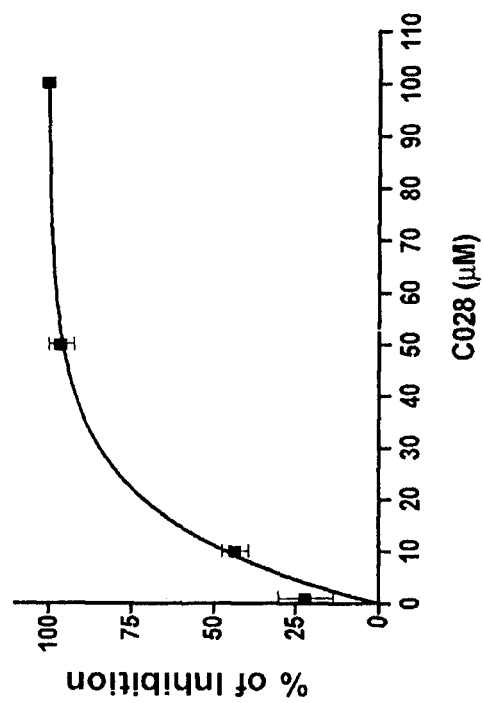
Figure 2C:
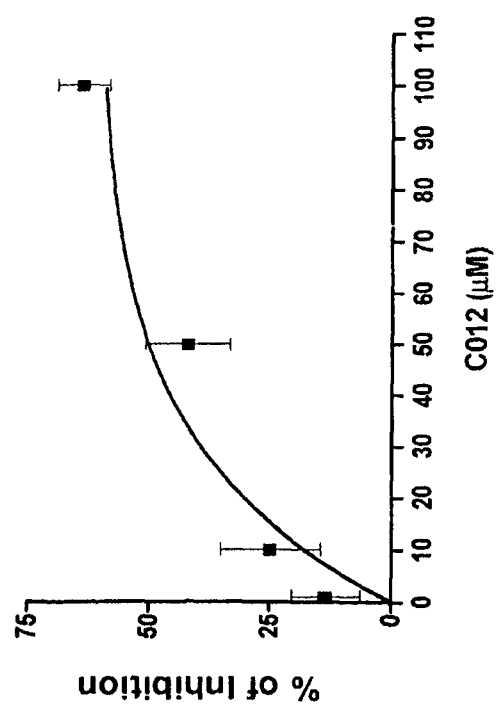

Effect of Compounds 001-029 on Phosphate Uptake Inhibition in Caco-2 Human Intestinal Epithelial Cells Caco-2 cells were cultured in DMEM medium containing 20% Fetal Bovine Serum. Medium from the sub-confluent monolayer of Caco-2 cells was removed. The resulting cells were washed with either a sodium free buffer (137 mM choline chloride, 5.4 mM KCl, 2.8 mM $CaCl_2$, 1.2 mM $MgSO_4$, and 14 mM Tris-HCl at pH 7.4), or with a buffer that contained sodium (137 mM sodium chloride, 5.4 mM KCl, 2.8 mM $CaCl_2$, 1.2 mM $MgSO_4$, and 14 mM Tris-HCl at pH 7.4). After the wash, sodium or sodium free buffer comprising 1 µM of radiolabeled phosphate ($K_2H^{32}PO_4$, 1 µCi/mL) and 100 µM of a small molecule having a phosphate group that was selected from the group containing Compounds 001-029 was added to the cells and they were incubated for 20 min at 37° C. Phosphate uptake was terminated by removing the uptake media and washing the cells with an ice-cold solution of 14 mM Tris-HCl, pH 7.4 that contained 137 mM of either choline chloride or sodium chloride. The monolayers of the cells were solubilized by the addition of a 1% solution of Triton X-100 to extract the radiolabeled phosphate. Aliquots of the radiolabeled phosphate were added to scintillation fluid and the radioactivity was determined by liquid scintillation counting. The difference between the assays using the two solutions with or without sodium represents the sodium dependent transport of phosphate. FIG. 1 shows that, with the exception of C-003, 014, 016, and 018, the small molecules having a phosphate group reduced or completely inhibited the uptake of phosphate in Caco-2 human epithelial cells.

Example 2

Effect of the Dosage of Small Molecule Compounds Having a Phosphate Group on Phosphate Uptake Inhibition The procedure of example 1 was repeated using C-002, C-004, C-012, and C-028 at concentrations from 1 to 100 µM. The results were recorded as the percent of phosphate uptake inhibition versus concentration of the small molecule having a phosphate group. FIG. 2 shows that the percent inhibition of phosphate uptake in Caco-2 cells increased with the concentration of the small molecule compound having a phosphate group until a limiting concentration was reached.

Example 3

Figure 3:
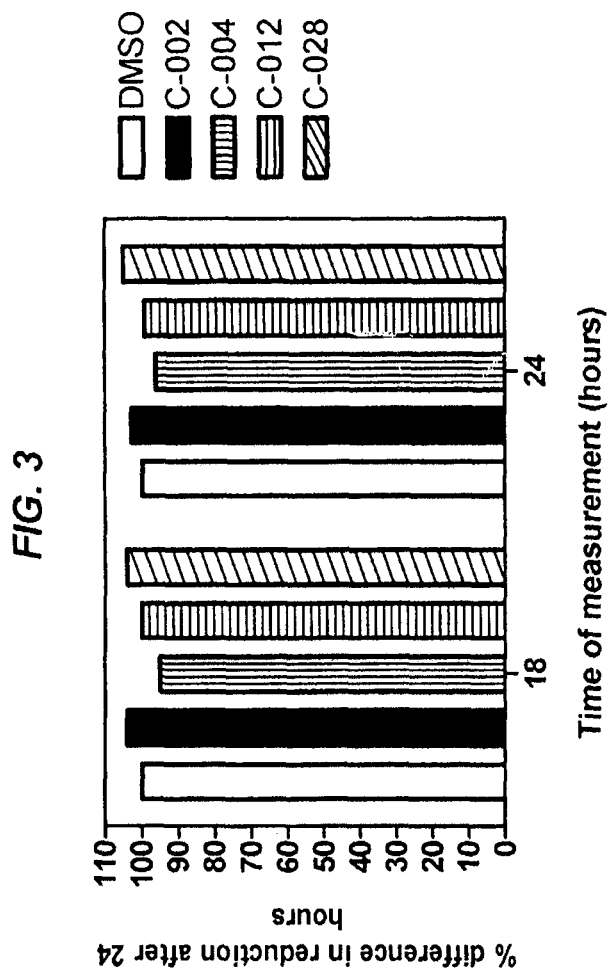
FIG. 3 shows the viability of Caco-2 human intestinal epithelial cells in the presence of Compounds 002, 004, 012, and 028 using ALAMAR BLUE stain reduction.

Determination of the Toxicity of Small Molecule Compounds Having a Phosphate Group in the Phosphorus Transport Assay Staining was performed with ALAMAR BLUE stain in the presence of 100 µM C-002, C-004, C-012, and C-028 cells to exclude compound toxicity in the phosphorus transport assay. Caco-2 cells were plated into a 96-well plate in concentrations which gave about 16,000 cells/well on the day of the test (e.g., 8000 cells/well for a 1 day growth, 4000 cells/well for a 2 day growth, 2000 cell/well for a 3 day growth). On the day of the test, old media was replaced by 80 µL of fresh media per well with either a 100 µM final concentration of the small molecule having a phosphate group in DMSO, or with 1% of DMSO in the control wells. Testing was performed in duplicate. ALAMAR BLUE stain (BioSource International, Inc., Cat#DAL1100) was added at a final concentration of 10% into each well according to manufacturer instructions. The cells were then incubated at 37° C. for another 18 or 24 hours, and the reduction of ALAMAR BLUE stain by vital cells was measured spectrophotometrically at 570 nm and 600 nm. The results were calculated as the percent of reduction using the formula in the manufacturer's manual (TREK Diagnostic Systems, PI-DIAL 1025/1100 Rev 1.0). FIG. 3 shows that the percent difference in ALAMAR BLUE stain reduction after 18 and 24 hours was virtually unchanged, indicating that the small molecules having a phosphate group were nontoxic to the Caco-2 human epithelial cells.

Figure 4:
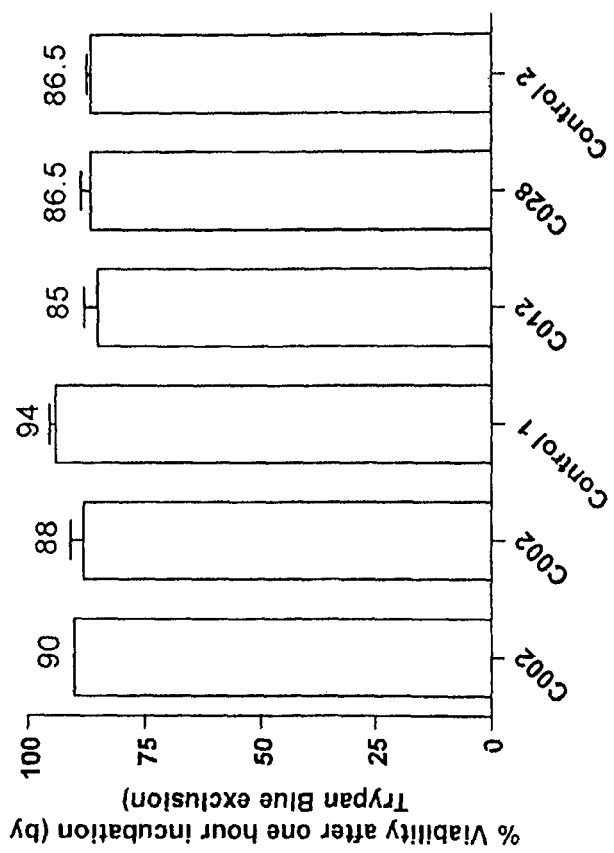
FIG. 4 shows the viability of Caco-2 human intestinal epithelial cells in the presence of Compounds 002, 004, 012, and 028 using trypan blue exclusion.

Trypan blue exclusion was used to determine the effect of C-002, 004, 012, and 028 on cell viability. The cells were plated in the same way as the ALAMAR BLUE stain test (see above). On the day of the test, media was removed, cells were washed with PBS and incubated with 100 µM (final concentration) of C-002, C-004, C-012 and C-028 in either a sodium free buffer (137 mM choline chloride, 5.4 mM KCl, 2.8 mM $CaCl_2$, 1.2 mM $MgSO_4$, and 14 mM Tris-HCl at pH 7.4), or with a buffer that contained sodium (137 mM sodium chloride, 5.4 mM KCl, 2.8 mM $CaCl_2$, 1.2 mM $MgSO_4$, and 14 mM Tris-HCl at pH 7.4). Testing was performed in duplicate. After 1 hour of incubation the cells were detached with trypsin/EDTA, transferred to an Eppendorf tube, and their viability was counted using 0.4% trypan blue stain (Invitrogen, Cat.#15250-061) in a 1:4 dilution with confocal microscopy. FIG. 4 shows that the small molecules having a phosphate group had no significant effect on the viability of the Caco-2 human epithelial cells after one hour of incubation.

Example 4

Figure 5:
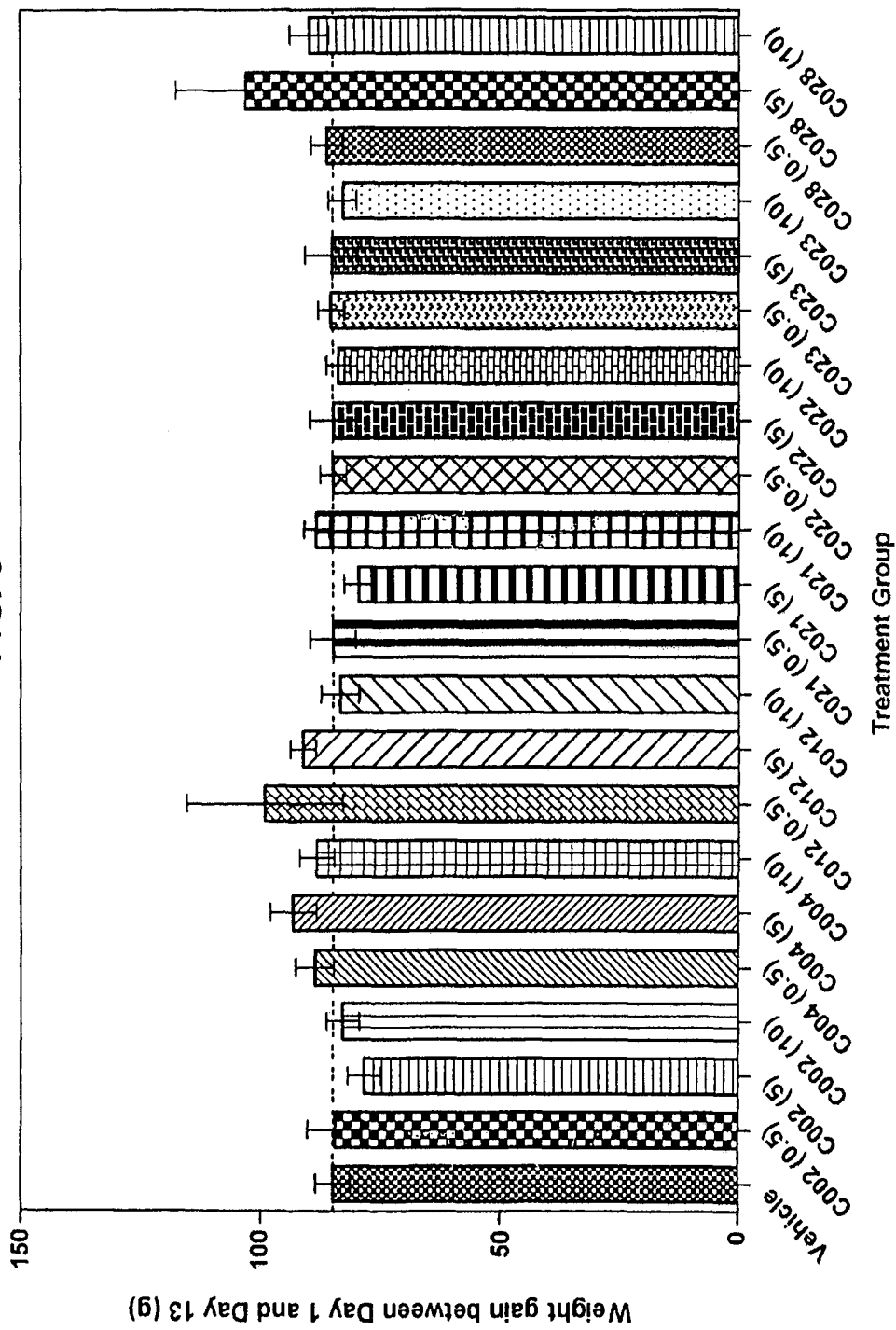
FIG. 5 shows the dosage effect of Compounds 002, 004, 012, 021, 022, 023, and 028 on male Sprague Dawley rats.

Determination of the Maximum Tolerated Dose (MTD) of Small Molecules Having a Phosphate Group for Male Sprague Dawley Rats Male Sprague Dawley rats were given C-002, C-004, C-012, C-021, C-022, C-023, and C-028 orally and daily at doses of 0.5, 5 and 10 mg per kg for twelve days. The mortality and animal weight data were recorded. No death was accounted and no significant effect on weight gain was observed (see FIG. 5). These results suggest no or low toxicity of these compounds when administered to up to 10 mg/kg.

Example 5

Efficacy of Compounds Represented by Structural Formulas I-XXXII on the Reduction of Serum Phosphate The efficacy of compounds represented by Structural Formulas I-XXXII on reducing serum phosphate levels is tested in uremic rats. To induce kidney failure and elevation of serum phosphate levels, male Sprague Dawley rats are administered orally and daily, adenine (500 mg/kg/day), for a period of twelve days. In the same gavage solution, compounds represented by Structural Formulas I-XXXII are administered orally and daily at doses ranging from 0.5 to 10 mg/kg. During the study, 25 g of a high phosphate diet is offered daily, immediately after oral gavage, for a restricted period of time (e.g., three hours). Blood is collected at days 1, 6 and 12. Intestines are collected at day 12. Serum phosphate and FGF-23 levels are measured and the NaPi-2b transcript is quantified from the intestine. Serum phosphate levels are expected to be reduced during the course of the study. Reduced serum phosphate should result in an elevation of serum FGF-23 and elevation in intestinal NaPi-2b transcription.

Example 6

Preparation of Compound 002 (Scheme 1)

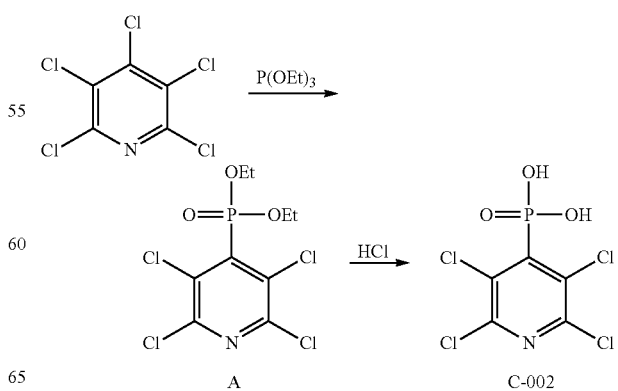

A 100 mL, 4-necked round bottom flask was charged with 2,3,4,5,6-pentachloropyridine (10 g, 0.0397 mol) and triethyl phosphite (6.8 g, 0.0409 mol) under nitrogen. The reaction mixture was heated to reflux, maintained for 24 h, and then brought to 25-30° C. Water (50 mL) was added to the reaction mixture and extraction occurred with EtOAc (2×50 mL). The combined organic extracts were dried over $MgSO_4$ and concentrated under vacuum to afford crude material. The crude material was purified by column chromatography (Silicagel 100-200) with DCM (900 mL) as the eluent. The pure column fractions were combined and evaporated under vacuum to give a cream colored solid (3.8 g, 27% yield). $^1H$ NMR was performed on the cream colored solid and the spectrum was consistent with Compound A.

A 100 mL, 4-necked round bottom flask was charged with Compound A (1.5 g, 0.0042 mol) and 6 M hydrochloric acid (50 mL). The reaction mixture was heated to reflux, maintained for 4 h, brought to 25-30° C., and concentrated under vacuum. Water (30 mL) was added to the reaction mixture and the solution was concentrated under vacuum. Acetone (50 mL) was then added to the reaction mixture and the solution was concentrated under vacuum. Dichloromethane (30 mL) was added to the reaction mixture and the solution was stirred for 15 min at 25-30° C. The compound was precipitated, filtered, and the slurry was washed with n-hexane (30 mL) to give C-002 (1.2 g, 95% yield) as an off-white solid. C-002 was characterized by $^1H$ NMR, $^{13}C$ NMR, and $^{31}P$ NMR. $^1H$ NMR (DMSO-d6): δ 5.00-7.00 ppm (bs, 2H). $^{13}C$ NMR (DMSO-d6): δ 146.87, 146.76, 146.17, 144.85, 131.28, 131.26. $^{31}P$ NMR (DMSO-d6): δ 0.65 (s). The purity of C-002 was determined to be 98.3% by HPLC. MS (m/z): calcd. for $C_5H_2Cl_4NO_3P$, 296.9; found (M-1), 295.9.

Example 7

Preparation of Compound 004 (Scheme 2)

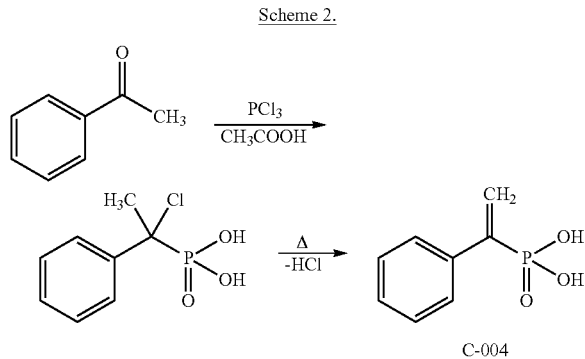

C-004

A 250 mL, 4-necked round bottom flask was charged with acetophenone (25 g, 0.208 mol) under nitrogen. Phosphorus trichloride (22.4 mL, 0.256 mol) and acetic acid (60 g, 0.999 mol) were added to the flask in sequence at 25-30° C. and stirred for 2 h. The reaction mixture was cooled to 0-5° C. and dry hydrochloric acid gas was passed through the reaction mixture at 0-5° C. for 1.5 h. The reaction mixture was brought to room temperature and stirred for an additional 14 h. The precipitated compound was filtered off and the slurry was washed with ether (100 mL). The compound was placed in a 100 mL round bottom flask, heated to 190° C., and maintained at that temperature for 15 min. The compound was then cooled to 60° C., chloroform (20 mL) was added to the flask, and the solution was stirred for 15 min at 25-30° C. The precipitated solid was filtered and dried at 50° C. to give C-004 (3 g, 8% yield) as on off-white solid. C-004 was characterized by $^1H$ NMR, $^{13}C$ NMR, $^{31}P$ NMR, and FT-IR. $^1H$ NMR (CD$_3$OD): δ 7.6 (m, 2H), 7.35 (m, 3H), 6.20 (s, 1H), 6.16 (s, 1H), 6.04 (s, 1H), 5.96 (s, 1H). $^{13}C$ NMR (CD$_3$OD): δ 145.16, 143.77, 139.00, 138.90, 129.29, 129.12, 129.06, 129.04, 128.70, 128.65. $^{31}P$ NMR (CD$_3$OD): δ 13.30, 13.10. The purity of C-004 was determined to be 98.4% by HPLC. MS (m/z): calcd. for $C_8H_9O_3P$, 184.13; found (M-1), 183.1.

Example 8

Preparation of Compound 012 (Scheme 3)

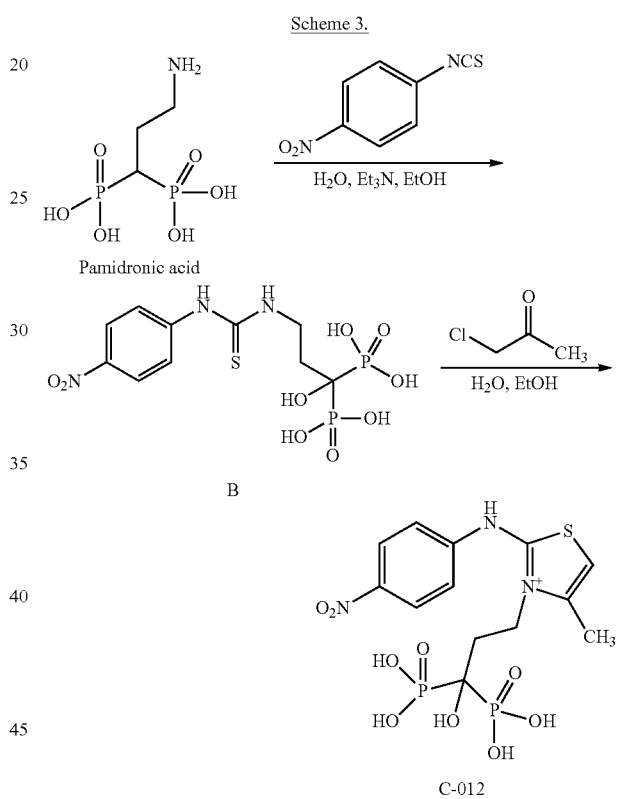

Palmidronic acid (4.7 g, 0.021 mol) was dissolved in a mixture of water (10 mL), triethylamine (12 mL) and ethanol (40 mL). The reagent, 4-nitrophenylisothiocyanate (3.96 g, 0.0219 mol) was added to the reaction mixture at 25-30° C. The reaction mixture was stirred for 16 h, heated to reflux, and maintained for 1 h. After the mixture was cooled to 5-10° C., 20% hydrochloric acid (20 mL) was added and the reaction was stirred at 25-30° C. for 14 h. The resulting solid precipitate was filtered and washed with water, ethanol, and acetone. The precipitate was dried in a hot air oven at 60-65° C. for 4 h to give Compound B (4.5 g, 50% yield). Compound B was characterized by $^1H$ NMR.

A 100 mL, 4-necked round bottom flask was charged with Compound B (2.25 g, 0.0054 mol), ethanol (35 mL), and water (6 mL), under nitrogen. Triethylamine (1.2 mL) was added to reaction mixture and stirred for 10 min at 25-30° C. Chloroacetone (90% solution, 0.74 g, 0.457 mL, 0.0056 mol) was added to the reaction at 25-30° C. The reaction mixture was heated to reflux, maintained for 1 h, and then brought to 25-30° C. Hydrochloric acid (20%, 1.2 mL) was added to the reaction mixture at 25-30° C. and stirred for 1 h. The reaction mixture was cooled to 10-15° C. and stirred for an additional 1 h. The precipitate was filtered, the slurry was washed with ethanol (15 mL) and acetone (20 mL), and the wet compound was dried at 50-60° C. for 2 h to give C-012 (1.15 g, 47% yield) as a light yellow solid. C-012 was characterized by $^1$H NMR. $^1$H NMR (CD$_3$OD): δ 8.4 (d, 2H), 7.85 (d, 2H), 6.8 (s, 1H), 4.65 (s, 2H), 2.6 (m, 2H), 2.45 (s, 3H). The purity of C-012 was determined to be 97.7% by HPLC. MS (m/z): calcd. for $C_{13}H_{18}N_3O_9P_2S^+$, 454.31; found (M+), 454.2.

Example 9

Preparation of Compound 021 (Scheme 4)

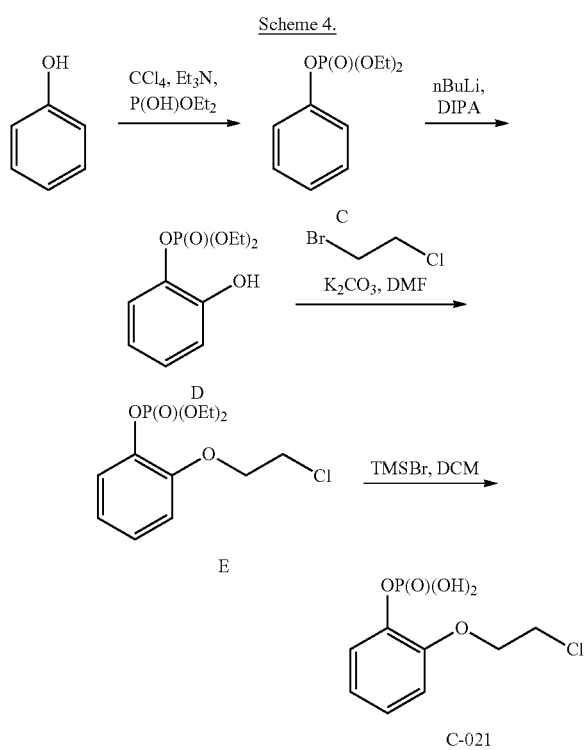

To a stirred solution of phenol (15 g, 159.5 mmol) in anhydrous CCl$_4$ (50 ml) was added freshly distilled triethylamine (16.94 g, 24 mL, 167.48 mmol) followed by diethylphosphite (23.129 g, 167.48 mmol) under an argon atmosphere. The reaction mixture was stirred for 2 h at room temperature and the disappearance of the starting materials was followed by TLC. Water was then added to the reaction mixture, which was subsequently diluted with DCM. The DCM layer was separated out, dried with brine, dried over anhydrous Na$_2$SO$_4$ filtered, and concentrated in vacuo to afford a colorless oil. This oil was dissolved in DCM (20 mL), loaded onto a silica gel column (230 mesh, 275 g), and gradient eluted with 0-50% EtOAc in hexane. Fractions were analyzed by TLC/UV, and the pure fractions were combined and concentrated in vacuo to dryness to give pure Compound C (30.40 g, 89% yield) as a colorless oil. TLC was performed in 30% EtOAc in hexane and Compound C was visualized with UV and PMA at R$_f$ 0.40.

To a stirred solution of solution of DIPA (9.67 g, 95.53 mmol) in anhydrous THF (200 mL) was added nBuLi (6.12 g, 95.53 mmol) at −20° C., and the reaction was stirred for an additional 30 min at −20° C. Compound C (20 g, 86.88 mmol) in THF (50 mL) was then added to the reaction mixture and it was stirred at rt for 2 h. When the starting materials had disappeared (as monitored by TLC), water was added to the reaction mixture and then EtOAc. The EtOAc layer was separated out, dried with brine, dried over anhydrous Na$_2$SO$_4$, filtered, and concentrated in vacuo to afford a colorless oil. This oil was dissolved in DCM (20 mL), loaded onto a silica gel column (230 mesh, 275 g), and gradient eluted with 0-100% EtOAc in hexane. The column fractions were analyzed by TLC/UV. The pure fractions were combined and concentrated in vacuo to dryness to give pure Compound D (16.12 g, 75% yield) as a colorless oil. TLC was performed in 30% EtOAc in hexane and Compound D was visualized with UV and PMA at R$_f$ 0.30.

To a stirred solution of Compound D (5 g, 95.53 mmol) in anhydrous DMF (200 mL) was added K$_2$CO$_3$ (6.0 g, 43.44 mmol) and 1-bromo-1-chloroethane (3.11 g, 21.72 mmol) under an argon atmosphere at rt. The reaction mixture was stirred for 24 h and the disappearance of the starting materials was monitored by TLC. Water was then added to the reaction mixture, followed by EtOAc. The EtOAc layer was separated out, dried with brine, dried over anhydrous Na$_2$SO$_4$, filtered, and concentrated in vacuo to afford a colorless oil. This oil was dissolved in DCM (20 mL), loaded onto a silica gel column (230 mesh, 275 g) and gradient eluted with 0-100% EtOAc in hexane. The column fractions were analyzed by TLC/UV. The pure fractions were combined and concentrated in vacuo to dryness to give pure Compound E (16.12 g, 75% yield) as a colorless oil. TLC was performed in 50% EtOAc in hexane and Compound E was visualized with UV and PMA at R$_f$ 0.25.

To a stirred solution of Compound E (5 g, 16.19 mmol) in anhydrous DCM (50 mL) was added TBS-Br (15.69 g, 97.18 mmol) under an argon atmosphere at rt. The reaction mixture was stirred for 2 h and the disappearance of the starting materials was monitored by TLC. Water was then added to the reaction mixture and then acetone. The organic solvent was removed by rotary evaporation to give a water-insoluble, white precipitate. The solid crystalline product was filtered, washed thoroughly with water, and dried under high vacuum to give C-021 as an off-white crystalline solid (3.0 g, 75% yield). TLC was performed in 100% EtOAc and C-021 was visualized with UV and PMA at R$_f$ 0.15. C-021 was characterized by $^1$H NMR and $^{31}$P NMR. $^1$H NMR (300 MHz, DMSO-d6): 3.9 (dd, J=6.0, 5.7 Hz, 2H), 4.28 (dd, 5.4, 5.7 Hz, 2H), 7.0 (m, 1H), 7.10 (m, 1H), 7.45 (m, 1H), 7.65 (m, 1H). $^{31}$P NMR (300, DMSO-d6): 11.669 (s). MS (m/z): calcd. for $C_8H_{10}ClO_5P$, 252.59; found (M$^+$-OH), 235.1.

Example 10

Preparation of Compound 022 (Scheme 5)

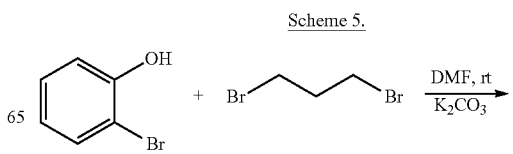

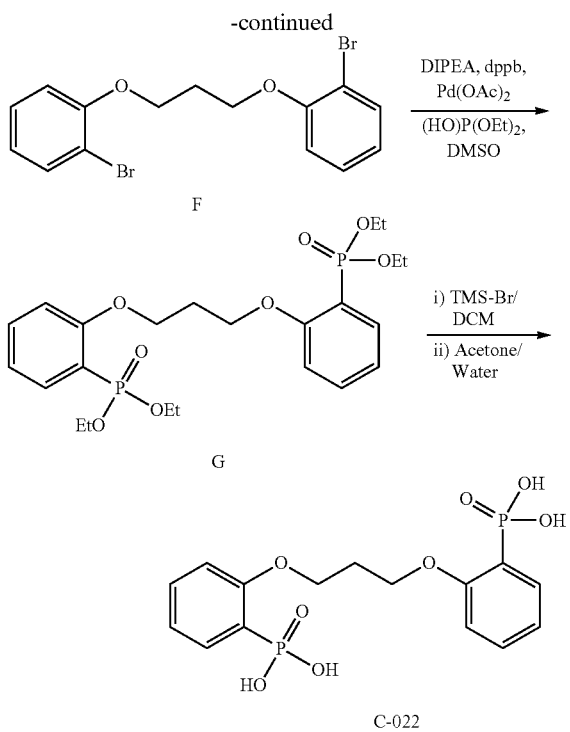

C-022

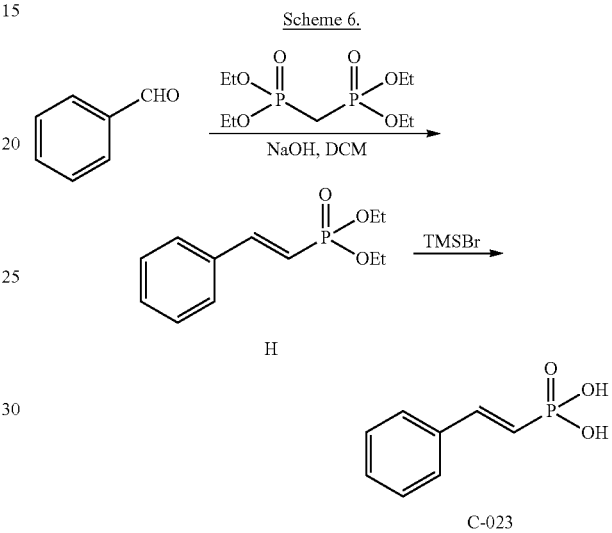

Scheme 6.

H

C-023 traces of DMF and EtOH. $^1$H NMR (200 MHz, DMSO-$d_6$): δ 2.16 (p, J=6.0 Hz, 2H), 4.24 (t, J=6.0 Hz, 4H), 6.94 (dt, J=7.6, 3.2 Hz, 2H), 7.05 (t, J=8.2 Hz, 2H), 7.43 (t, J=8.0 Hz, 2H), 7.63 (dd, J=14.2, 7.4 Hz, 2H); $^{13}$C NMR (75 MHz, DMSO-$d_6$): 28.3, 64.7, 112.3, 112.4, 119.6, 119.7, 120.5, 122.0, 133.1, 133.2, 133.3, 160.0; Mass: 388.9 (M$^+$+1). The purity of C-022 was determined to be 99.5% by HPLC.

Example 11

Preparation of Compound-023 (Scheme 6)

To a suspension of 2-bromophenol (25 g, 0.144 mol) and potassium carbonate (60 g, 0.433 mol) in DMF (175 ml), 1,3-dibromopropane (7.0 ml, 0.069 mol) was added dropwise at rt under a nitrogen atmosphere. The reaction mixture was stirred at rt for 5 h. After completion of reaction (as monitored by TLC), the reaction mixture was diluted with water (820 mL) and stirred for 15 min. The precipitated white solid was filtered, washed with water, and air dried to afford Compound F (25 g, 89% yield). $^1$H NMR (200 MHz, DMSO-$d_6$): δ 2.21 (p, J=6.4 Hz, 2H), 4.24 (t, J=6.4 Hz, 4H), 6.87 (dt, J=7.4, 1.4 Hz, 2H), 7.14 (dd, J=8.0, 1.4 Hz, 2H), 7.32 (dt, J=8.0, 1.4 Hz, 2H), 7.55 (dt, J=7.8, 1.4 Hz, 2H).

To a solution of Compound F (23 g, 59.0 mmol) in DMSO (160 mL), DIPEA (83 mL), dppb (4.05 g, 9.4 mmol), palladium(II) acetate (2.1 g, 9.4 mmol) and diethyl phosphite (38.2 mL, 295 mmol) were added at rt under a nitrogen atmosphere. The reaction mixture was heated overnight at 100° C. The reaction mixture was then cooled to rt, diluted with 2N HCl (300 mL), and extracted with ethyl acetate (2×300 mL). The organic layer was washed with water (250 mL), dried with brine (200 mL), dried over sodium sulfate, and evaporated under reduced pressure. The resulting crude mass was purified by column chromatography using MeOH/DCM as the eluent to give Compound G (11.9 g, 40% yield). $^1$H NMR (200 MHz, CDCl$_3$): δ 1.24 (t, J=7.4 Hz, 12H), 2.33 (p, J=6.0 Hz, 2H), 3.96-4.17 (m, 8H), 4.34 (t, J=6.0 Hz, 4H), 6.94-7.04 (m, 4H), 7.48 (t, J=8.6 Hz, 2H), 7.80 (dd, J=15.0, 7.6 Hz, 2H); Mass: 500.9 (M$^+$+1).

To a solution of Compound G (10 g, 0.02 mol) in DCM (40 mL), TMS—Br (15.8 mL, 0.12 mol) was added slowly under a nitrogen atmosphere. The reaction mixture was stirred at rt for 4 h. After complete disappearance of Compound G (by mass), volatiles were removed under reduced pressure. Acetone-water (50 mL, 1:1) was added and the reaction mixture was stirred at rt for 30 min. The precipitated solids were filtered, washed with acetone, and re-precipitated from DMF-EtOH-EtOAc (1:3:4) to give C-022 (6.0 g, 77% yield). A final precipitation was done using DMSO-water (1:3) to remove To a stirred solution of benzaldehyde (3.34 g, 31.50 mmol) and bis-diethylphosphonate (9.08 g, 31.50 mmol) in anhydrous DCM (50 mL) was added 50% aqueous NaOH under an argon atmosphere at rt for 2 h. After the disappearance of the starting materials (monitored by TLC), water was added to the reaction mixture followed by additional DCM. The DCM layer was separated out, washed with dilute HCl, washed with water, dried with brine, dried over anhydrous Na$_2$SO$_4$, filtered and concentrated in vacuo to afford crude product. The crude product was dissolved in DCM (10 mL), loaded onto a silica gel column (230 mesh, 200 g), and gradient eluted with 0-75% ethyl acetate in hexane. Column fractions were analyzed with TLC/UV, and the pure fractions were combined and concentrated in vacuo to dryness to give pure Compound H (6.4 g, 85% yield) as a colorless oil. TLC was performed in 40% EtOAc/hexane and Compound H was visualized with UV and PMA at R$_f$ 0.45.

To a stirred solution of Compound H (3 g, 12.48 mmol) in anhydrous DCM (50 mL) was added TMS—Br (11.47 g, 94.92 mmol) under an argon atmosphere at rt. The reaction mixture was stirred for 2 h and the progress of the reaction was monitored by TLC. Water was then added to the reaction mixture, followed by acetone. The organic solvent was removed under reduced pressure to produce a water-insoluble, white precipitate. The precipitate was filtered, washed thoroughly with water, and dried under high vacuum to result in C-023 as a crystalline solid (1.83 g, 80% yield). TLC was performed in 100% EtOAc and C-023 was visualized with UV and PMA at R$_f$ 0.15. C-023 was characterized by $^1$H NMR and $^{31}$P NMR. $^1$H NMR (300 MHz, DMSO-d6): δ 6.5 (dd, J=18.0, 16.2 Hz, 1H), 7.2 (dd, J=17.7, 17.4 Hz, 1H), 7.4 (m, 3H), 7.6 (m, 2H), 9.6 (bs, 2H). $^{31}$P NMR (300 MHz, DMSO-d6): 14.707 (s). MS (m/z): calcd. for $C_8H_9O_3P$, 184.13; found (M+), 184.1.

Example 12

Preparation of Compound 28 (Scheme 7)

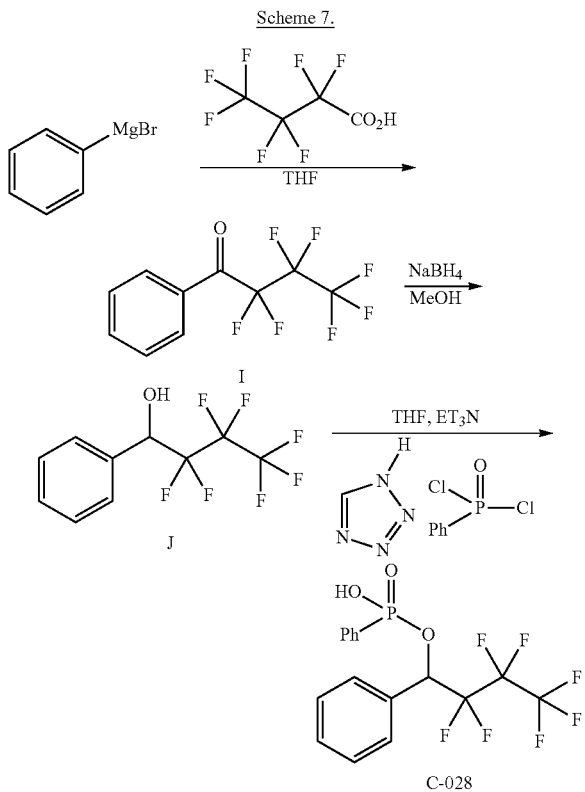

To a stirred solution of heptafluorobutyric acid (17 g, 79.42 mmol) in anhydrous THF (200 mL) was added PhMgBr (17.28 g, 95.30 mmol) under an argon atmosphere at −20° C. The reaction was stirred for 1 h at −20° C. and the disappearance of the starting materials was monitored by TLC. A saturated NH$_4$Cl solution was slowly added to the reaction mixture and the mixture was subsequently diluted with Et$_2$O. The Et$_2$O layer was separated out, washed with dilute HCl, washed with water, dried with brine, dried over anhydrous Na$_2$SO$_4$, filtered, and concentrated in vacuo to afford a colorless oil. The oil was dissolved in DCM (20 mL), loaded onto a silica gel column (230 mesh, 500 g) and gradient eluted with 0-20% ethyl acetate in hexane. The column fractions were analyzed by TLC/UV. The pure fractions were combined and concentrated in vacuo to dryness to give pure Compound I (5.44 g, 25% yield) as a colorless oil. TLC was performed in 15% EtOAc/hexane and Compound I was visualized with UV and PMA at R$_f$ 0.70.

To a stirred solution of Compound I (5.44 g, 19.84 mmol) in anhydrous MeOH (50 mL) was added NaBH$_4$ (0.9 g, 23.81 mmol) under an argon atmosphere at rt. The reaction mixture was stirred for 15 min and the disappearance of the starting materials was monitored by TLC. After the starting materials disappeared, a saturated solution of NH$_4$Cl was added to the reaction mixture, and it was subsequently diluted with EtOAc. The EtOAc layer was separated out, dried with brine, dried over anhydrous Na$_2$SO$_4$, filtered, and concentrated in vacuo to afford a colorless oil. This oil was dissolved in DCM (10 mL), loaded onto a silica gel column (230 mesh, 100 g), and gradient eluted with 0-30% EtOAc in hexane. Column fractions were analyzed by TLC/UV. The pure fractions were combined and concentrated in vacuo to dryness to give pure Compound J (4.65 g, 85% yield) as a colorless oil. TLC was performed in 15% EtOAc/hexane and Compound J was visualized with UV and PMA at R$_f$ 0.45.

To a stirred solution of Compound J (3 g, 10.86 mmol) in anhydrous THF (50 mL) under an argon atmosphere at rt was added Et$_3$N (1.64 g, 16.29 mmol) and tetrazole (0.91 g, 10.03 mmol), followed by dichlorophenylphosphonate. The reaction mixture was stirred for 2 h and the disappearance of the starting materials was monitored by TLC. After the starting materials disappeared, water was added to the reaction flask, stirred for 30 min, and the reaction mixture was diluted with EtOAc. The EtOAc layer was separated out, washed with water, dried with brine, dried over anhydrous Na$_2$SO$_4$, filtered, and concentrated in vacuo to afford crude product. The crude product was purified by reverse phase column chromatography (C18 mesh, 50 g) and gradient eluted with 0-100% acetonitrile in water. Column fractions were analyzed by TLC using 75% ethyl acetate in hexane, and the product was visualized with UV and PMA at R$_f$ 0.15. The pure fractions were combined and concentrated in vacuo to result in a water-insoluble crystalline solid. The solid was filtered and dried over high vacuum to give C-028 as a pure crystalline white solid (3.7 g, 82% yield). C-028 was characterized by $^1$H NMR and $^{31}$P NMR. $^1$H NMR (300 MHz, DMSO-d6): 7.2-7.6 (m, 10H), 6.0 (m, 1H), 5.4 (bs, 1H). $^{31}$P NMR (300 MHz, DMSO-d6): 15.99 (s). MS (m/z): calcd. for $C_{16}H_{12}F_7O_3P$, 416.23; found 415.1.

The foregoing description is given for clearness of understanding only, and no unnecessary limitations should be understood therefrom, as modifications within the scope of the invention may be apparent to those having ordinary skill in the art.

Throughout the specification, where compositions are described as including components or materials, it is contemplated that the compositions can also consist essentially of, or consist of, any combination of the recited components or materials, unless described otherwise.

The practice of a method disclosed herein, and individual steps thereof, can be performed manually and/or with the aid of electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed is:

1. A method for inhibiting the transport of phosphate across the membrane of human epithelial cells, comprising administering to a human subject in need of phosphate transport inhibition in an amount effective to achieve a beneficial therapeutic outcome a compound selected from the group consisting of Formulae:

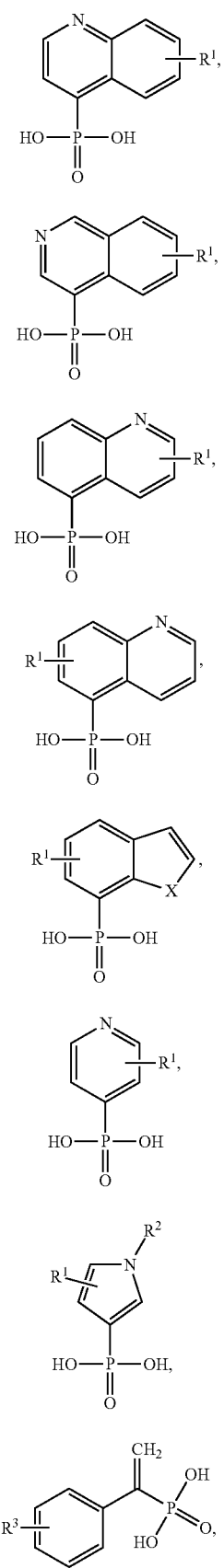
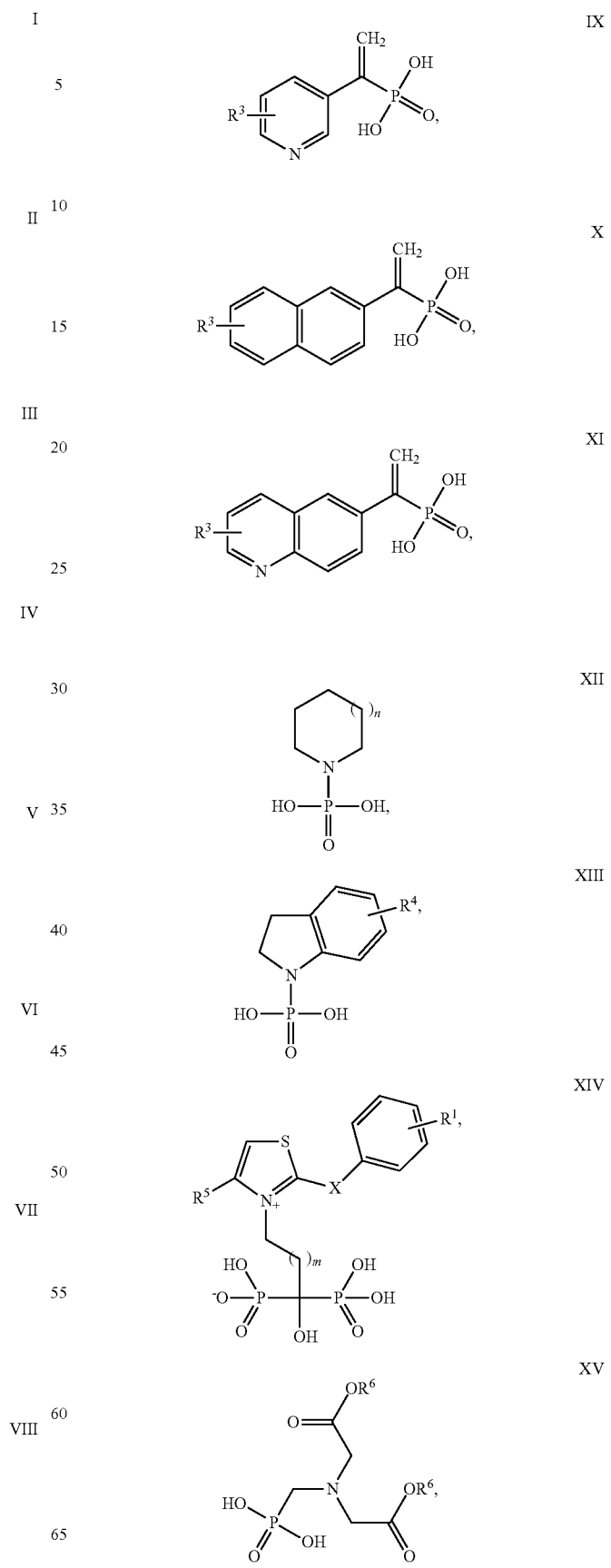

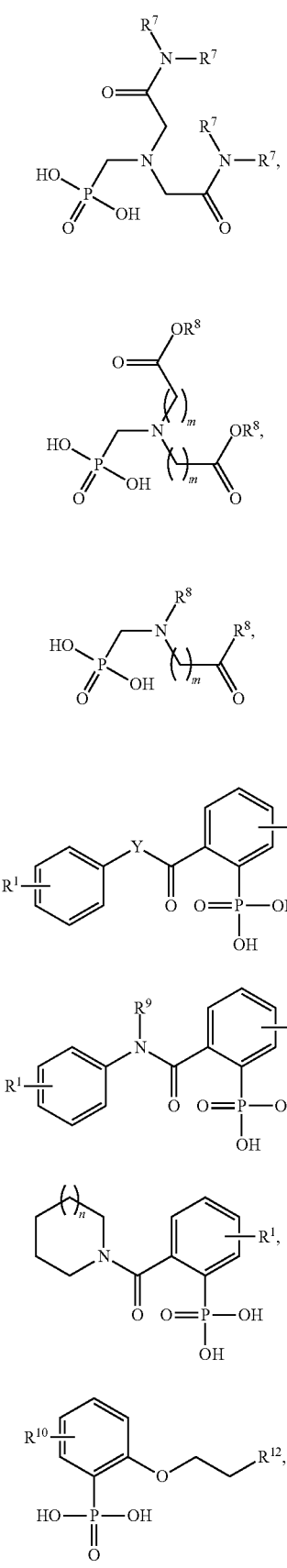
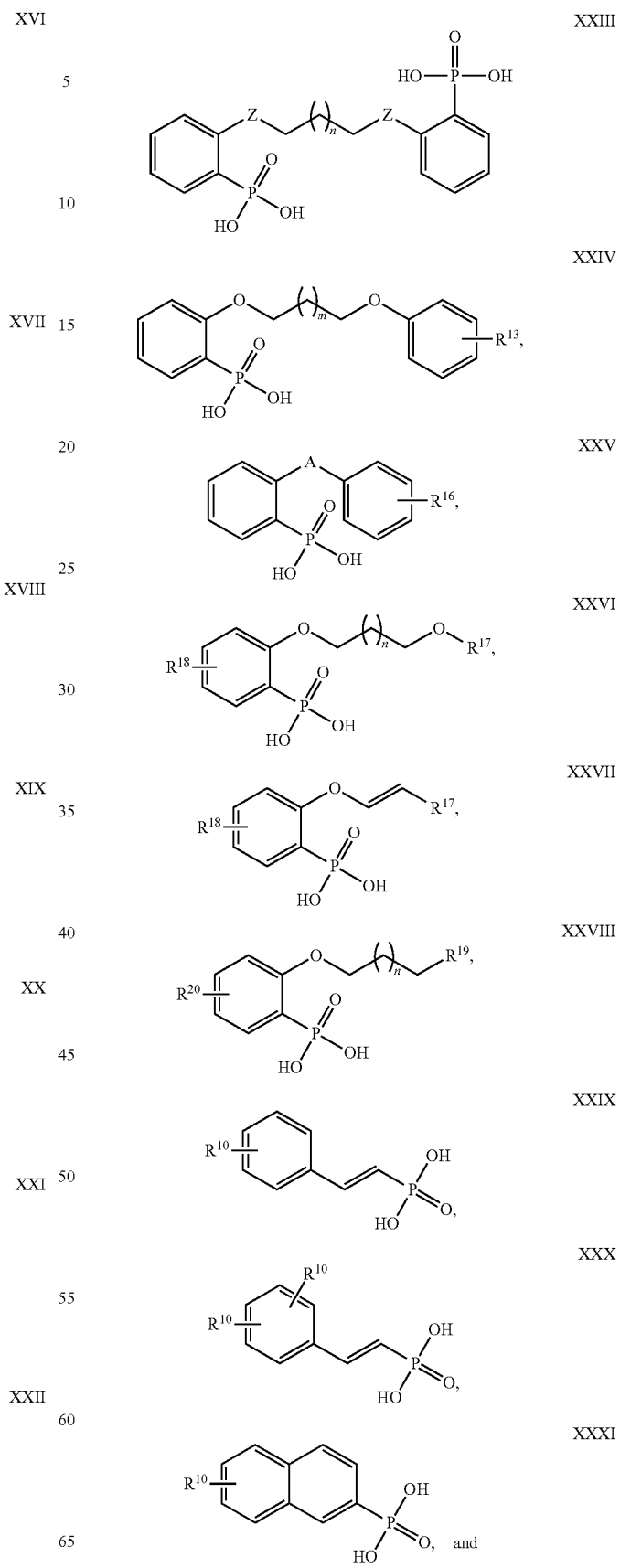

-continued

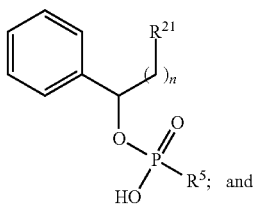
XXXII and a combination of any of the foregoing;
wherein

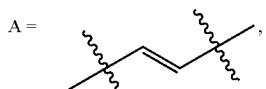

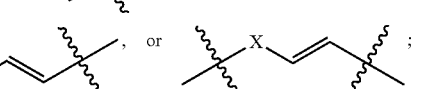

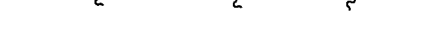

X is O, S, NH, or N-alkyl;
Y is O or S;
each Z independently is O, S, NH, or $CH_2$;
n is 0, 1 or 2;
m is 1 to 6;
$R^1$ is halogen, OH, O-alkyl, N-dialkyl, or NHCO-alkyl at single or multiple positions;
$R^2$ is H, alkyl, or substituted benzyl;
$R^3$ is halogen, alkyl, substituted benzyl, OH, O-alkyl, N-dialkyl, or NHCO-alkyl at single or multiple positions;
$R^4$ is H, halogen, O-alkyl, S-alkyl, N-dialkyl, or NHCO-alkyl;
$R^5$ is alkyl, aryl, or substituted aryl;
$R^6$ is alkyl, benzyl, or aromatic substituted benzyl;
$R^7$ is H, alkyl, benzyl, or aromatic substituted benzyl;
$R^8$ is H, alkyl, aryl, benzyl, or aromatic substituted benzyl;
$R^9$ is H or alkyl;
$R^{10}$ is hydrogen, alkyl, O-alkyl, S-alkyl, aryl, $NR^{11}{}_2$, or $NCOR^{11}$;
$R^{11}$ is alkyl or aryl;
$R^{12}$ is halogen;
$R^{13}$ is halogen, $OR^{14}$, $NR^{15}{}_2$, $PO_3H_2$, $SO_3H$, COOH, or $NH_2$;
$R^{14}$ is methyl, ethyl, isopropyl, tert-butyl, allyl, substituted benzyl, or unsubstituted benzyl;
$R^{15}$ is methyl, ethyl, isopropyl, allyl, substituted benzyl, or unsubstituted benzyl;
$R^{16}$ is $SO_3H$, COOH, or $NH_2$;
$R^{17}$ is methyl, ethyl, isopropyl, tert-butyl, cyclohexyl, aryl, or heteroaryl;
$R^{18}$ is methyl, ethyl, isopropyl, tert-butyl, halogen, OH, O-alkyl, N-dialkyl or NHCO-alkyl at single or multiple positions;
$R^{19}$ is halogen, $NR^{11}{}_2$, $NHCOR^{11}$, $SR^{11}$ or heteroaryl;
$R^{20}$ is halogen, methyl, ethyl, isopropyl, tert-butyl, $N(CH_3)_2$, $N(Et)_2$, $N(iPr)_2$, $NHCOCH_3$, $NHCOCF_3$, or NHCOPh; and, $R^{21}$ is alkyl, halogenated alkyl, O-alkyl, substituted aryl, or heteroaryl;

with the proviso that when n =0, $R^5$ =aryl, and $R^{21}$ is $CF_3$, then the phenyl ring of Formula XXXII is optionally substituted with fluorine; or a compound selected from the group consisting of

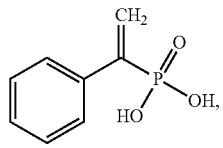
C-004

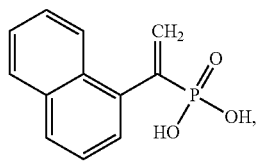
C-005

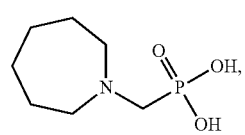
C-007

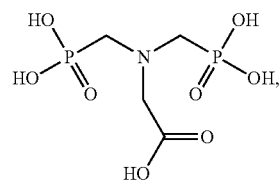
C-011

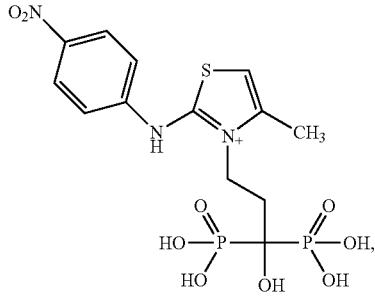
C-012

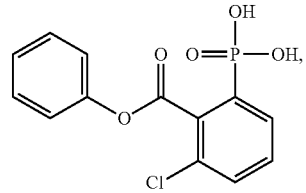
C-020

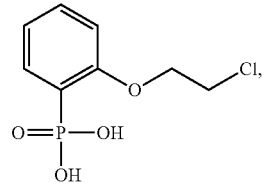
C-021

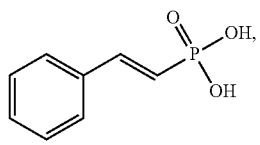
C-023

-continued

C-024
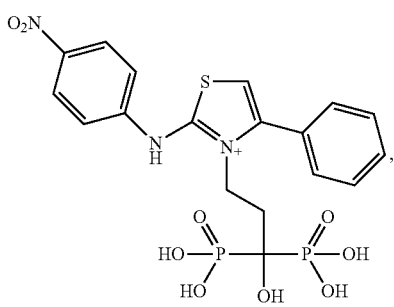

C-025
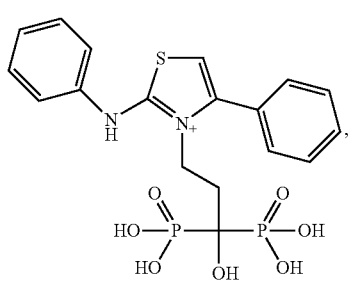

C-026
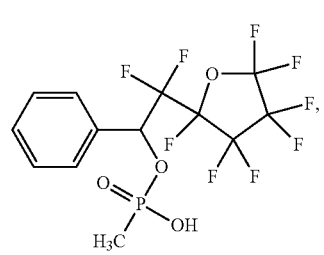

and

C-027
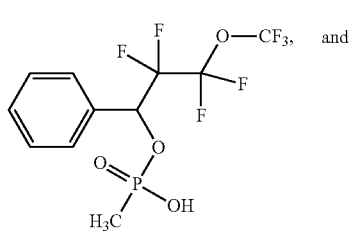

C-029
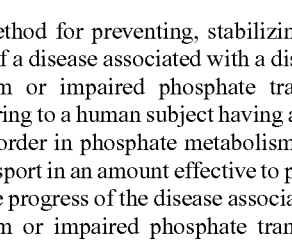

2. A method for preventing, stabilizing, or reversing the progress of a disease associated with a disorder in phosphate metabolism or impaired phosphate transport comprising administering to a human subject having a disease associated with a disorder in phosphate metabolism or impaired phosphate transport in an amount effective to prevent, stabilize, or reverse the progress of the disease associated with phosphate metabolism or impaired phosphate transport a compound selected from the group consisting of Formulae:

I
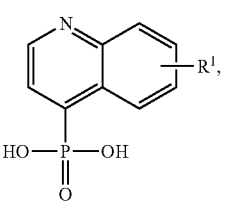

II
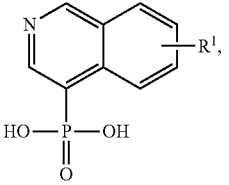

III
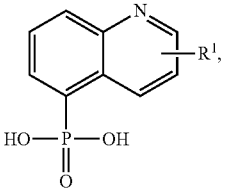

IV
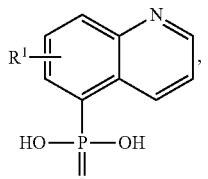

V
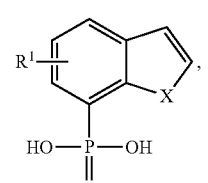

VI
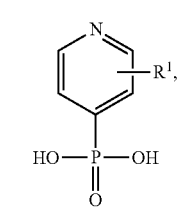

VII
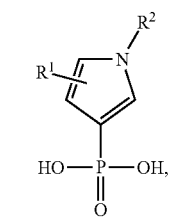

VIII
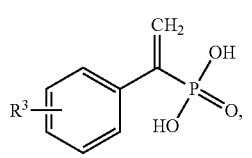

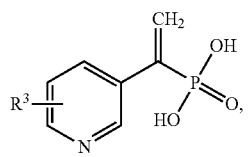
IX
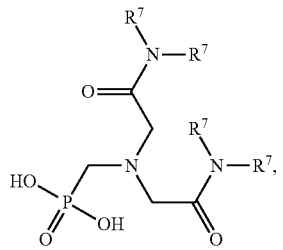
XVI
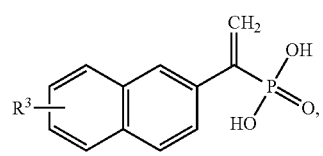
X
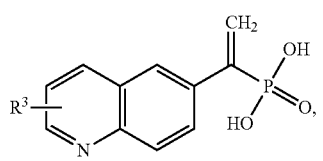
XI
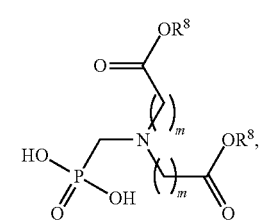
XVII
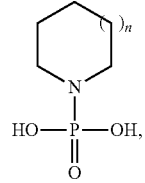
XII
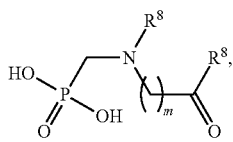
XVIII
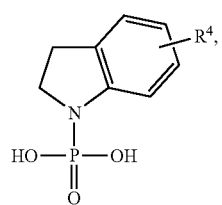
XIII
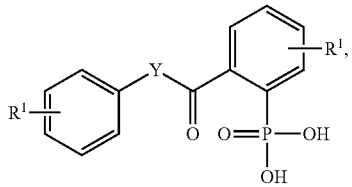
XIX
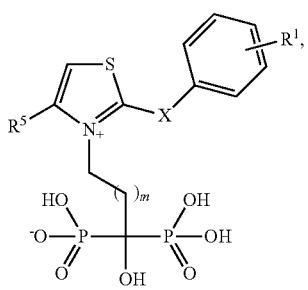
XIV
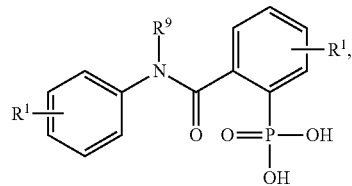
XX
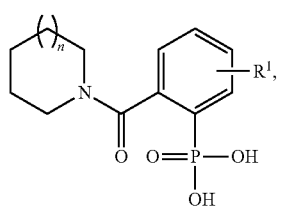
XXI
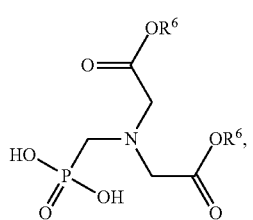
XV
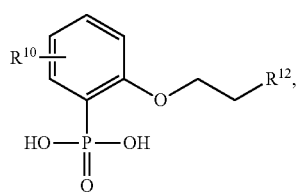
XXII XXIII 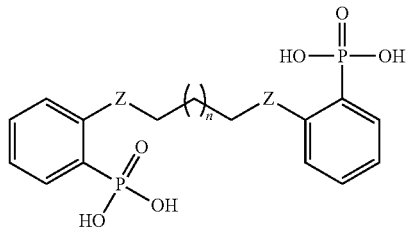

XXIV 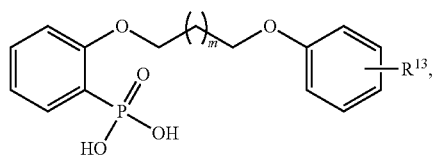

XXV 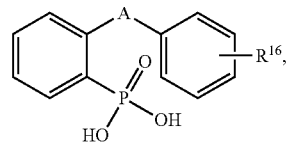

XXVI 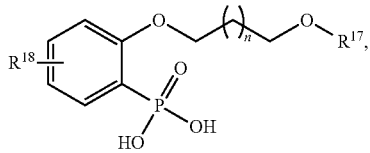

XXVII 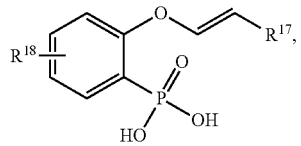

XXVIII 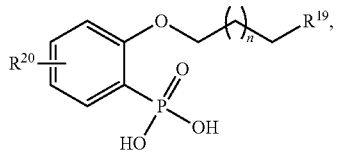

XXIX 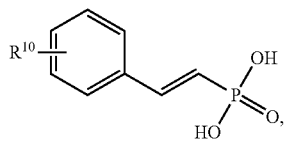

XXX 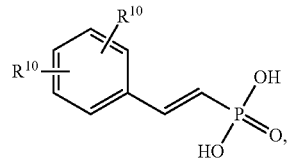

XXXI 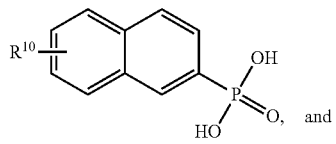, and

XXXII 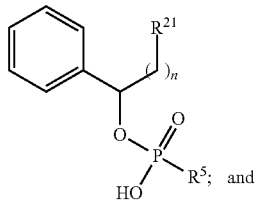

and a combination of any of the foregoing; wherein

A = 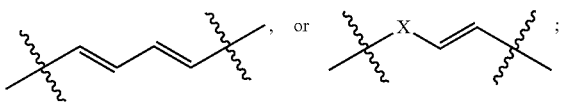

X is O, S, NH, or N-alkyl;
Y is O or S;
each Z independently is O, S, NH, or $CH_2$;
n is 0, 1 or 2;
m is 1 to 6;
$R^1$ is halogen, OH, O-alkyl, N-dialkyl, or NHCO-alkyl at single or multiple positions;
$R^2$ is H, alkyl, or substituted benzyl;
$R^3$ is halogen, alkyl, substituted benzyl, OH, O-alkyl, N-dialkyl, or NHCO-alkyl at single or multiple positions;
$R^4$ is H, halogen, O-alkyl, S-alkyl, N-dialkyl, or NHCO-alkyl;
$R^5$ is alkyl, aryl, or substituted aryl;
$R^6$ is alkyl, benzyl, or aromatic substituted benzyl;
$R^7$ is H, alkyl, benzyl, or aromatic substituted benzyl;
$R^8$ is H, alkyl, aryl, benzyl, or aromatic substituted benzyl;
$R^9$ is H or alkyl;
$R^{10}$ is hydrogen, alkyl, O-alkyl, S-alkyl, aryl, $NR^{11}_2$, or $NCOR^{11}$;
$R^{11}$ is alkyl or aryl;
$R^{12}$ is halogen;
$R^{13}$ is halogen, $OR^{14}$, $NR^{15}_2$, $PO_3H_2$, $SO_3H$, COOH, or $NH_2$;
$R^{14}$ is methyl, ethyl, isopropyl, tert-butyl, allyl, substituted benzyl, or unsubstituted benzyl;
$R^{15}$ is methyl, ethyl, isopropyl, allyl, substituted benzyl, or unsubstituted benzyl;
$R^{16}$ is $SO_3H$, COOH, or $NH_2$;
$R^{17}$ is methyl, ethyl, isopropyl, tert-butyl, cyclohexyl, aryl, or heteroaryl;
$R^{18}$ is methyl, ethyl, isopropyl, tert-butyl, halogen, OH, O-alkyl, N-dialkyl or NHCO-alkyl at single or multiple positions;
$R^{19}$ is halogen, $NR^{11}_2$, $NHCOR^{11}$, $SR^{11}$ or heteroaryl;
$R^{20}$ is halogen, methyl, ethyl, isopropyl, tert-butyl, $N(CH_3)_2$, $N(Et)_2$, $N(iPr)_2$, $NHCOCH_3$, $NHCOCF_3$, or NHCOPh; and,
$R^{21}$ is alkyl, halogenated alkyl, O-alkyl, substituted aryl, or heteroaryl;
with the proviso that when n =0, $R^5$=aryl, and $R^{21}$ is $CF_3$, then the phenyl ring of Formula XXXII is optionally substituted with fluorine; or a compound selected from the group consisting of 3. The method of claim 2, wherein the disease is selected from the group consisting of hyperparathyroidism, metabolic bone disease, uremic bone disease, renal bone disease, soft tissue calcification, cardiovascular calcification, cardiovascular events, calciphylaxis, and osteoporosis.

4. The method of claim 1, for the treatment or prevention of a disease wherein the accumulation of phosphate in serum can occur and comprising administering to a human subject in need of serum phosphate reduction or serum phosphate maintenance in an amount effective to reduce or maintain serum phosphate levels a compound according to claim 1.

5. The method of claim 4, wherein the disease is selected from the group consisting of hyperphosphatemia, chronic kidney disease, secondary hyperparathyroidism, hyperparathyroidism, and hypoparathyroidism.

6. The method of claim 5, for treating, delaying, or preventing hyperphosphatemia wherein the hyperphosphatemia results or would result from pharmaceutical intervention for the treatment of a disease in a human subject in need of such intervention, comprising administering to said human subject in an amount effective to treat, delay, or prevent hyperphosphatemia a compound according to claim 1.

7. The method of claim 6, wherein the pharmaceutical intervention is vitamin D based therapy.

8. The method of claim 6, wherein the disease is secondary hyperparathyroidism.

9. The method of claim 1, further comprising administering in combination at least two of said compounds.

10. The method of claim 1, wherein the compound is administered in a pharmaceutically acceptable formulation.

11. The method of claim 10, wherein the pharmaceutically acceptable formulation comprises a pharmaceutically acceptable carrier, diluent, exipient, or a mixture of any of the foregoing.

12. The method of claim 10, wherein the formulation is administered orally or by injection.

13. The method of claim 11, wherein the formulation is administered orally as an elixir, liquid, gel, syrup, slurry, capsule, tablet, or pill.

14. The method of claim 11, wherein the formulation is administered by injection subcutaneously, intravenously, or intraperitoneally.

15. The method of claim 1, wherein the compound is administered in dose of about 0.001 to about 1 gram per kilogram of body weight per day.

16. The method of claim 1, wherein the compound is selected from the group consisting of:

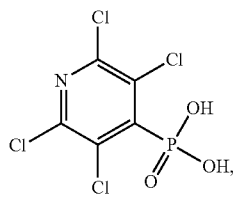
C-002

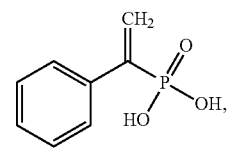
C-004

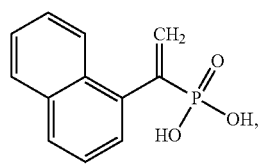
C-005

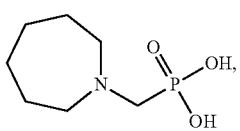
C-007

-continued

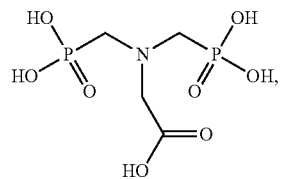
C-011

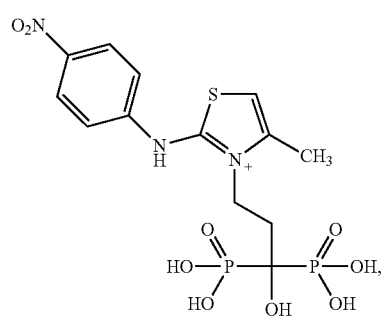
C-012

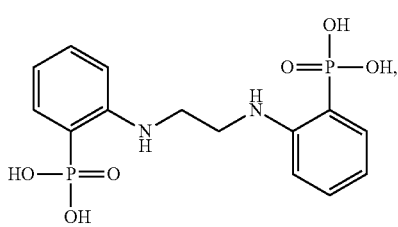
C-015

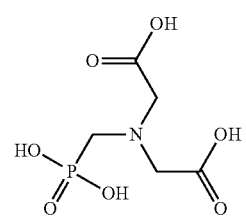
C-019

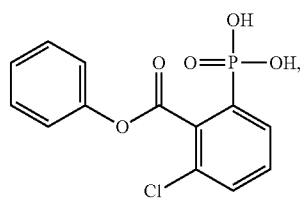
C-020

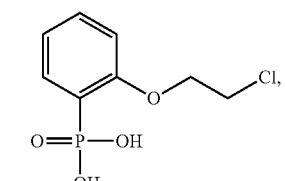
C-021

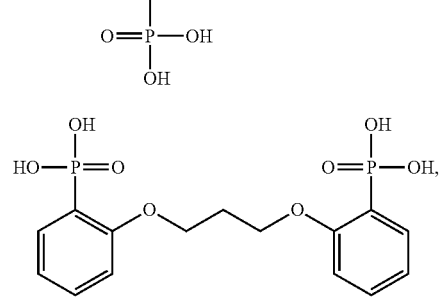
C-022

C-023
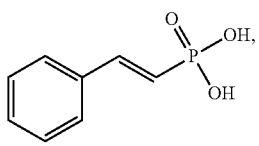
C-024
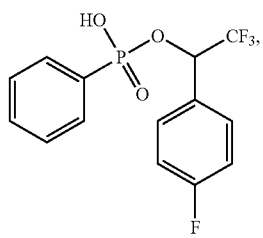 (with label C-029 showing phenyl-P(O)(OH)-O-CH(CF3)-phenyl-F)
and a combination of any of the foregoing.
17. The method of claim 16, wherein the compound is selected from the group consisting of:
C-025
C-002
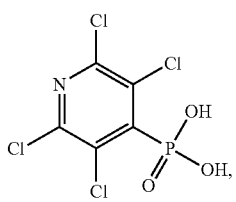
C-004
C-026
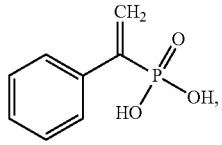
C-005
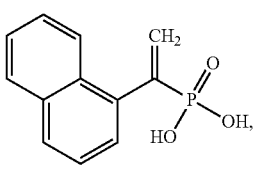
C-007
C-027
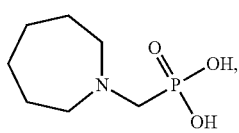
C-012
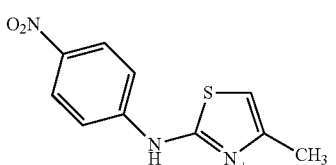
C-028
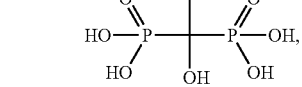
C-019
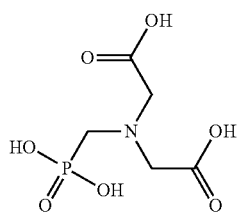

-continued
C-020
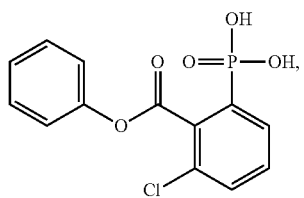
C-021
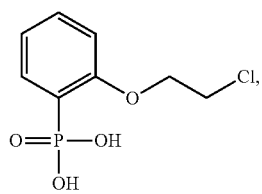
C-022
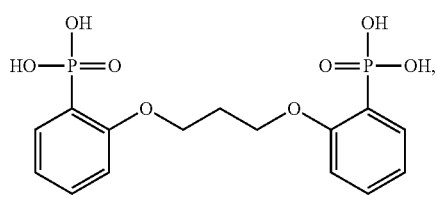
C-023
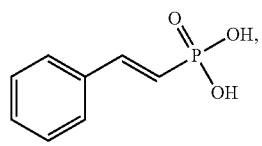
C-026
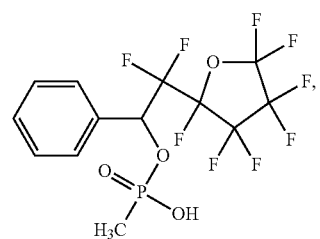
C-027
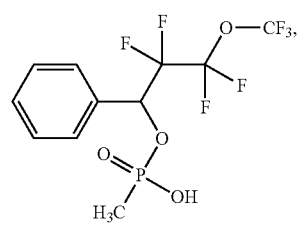
C-028
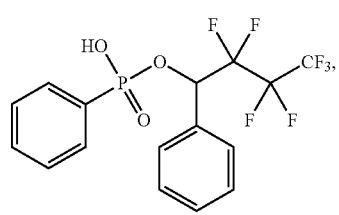
-continued
C-029
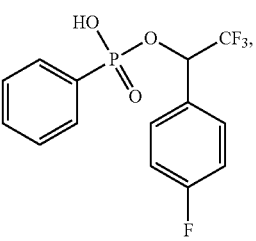
and a combination of any of the foregoing.
18. The method of claim 17, wherein the compound is selected from the group consisting of:
C-002
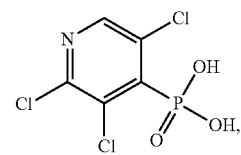
C-004
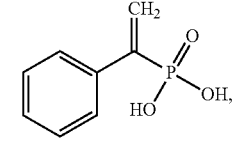
C-012
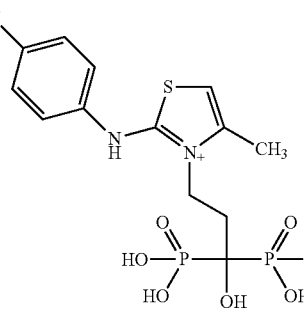
C-021
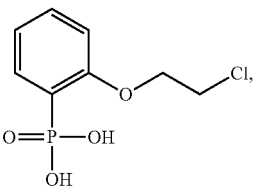
C-022
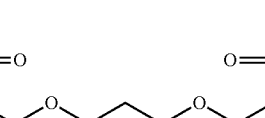
C-023
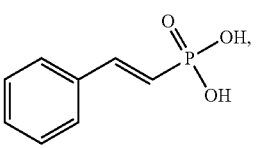

a combination of any of the foregoing.

19. A method for inhibiting the transport of phosphate across the membrane of human epithelial cells, comprising administering to a human subject in need of phosphate transport inhibition in an amount effective to achieve a beneficial therapeutic outcome a compound selected from the group consisting of:

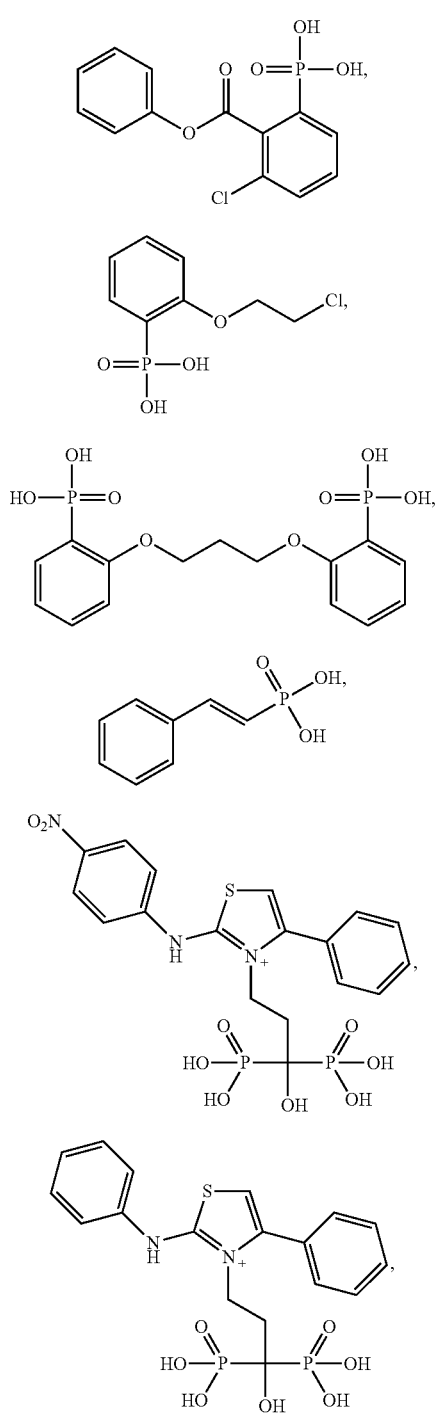
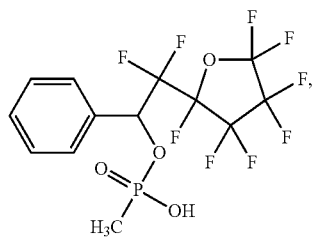
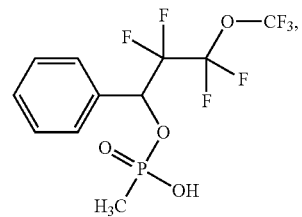
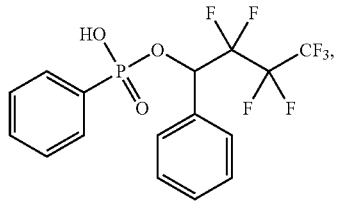
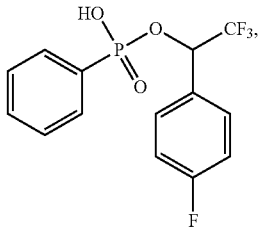
and a combination of any of the foregoing.
* * * * *